United States Patent
Alizon et al.

(10) Patent No.: US 7,029,679 B2
(45) Date of Patent: Apr. 18, 2006

(54) VARIANT OF LAV VIRUSES

(75) Inventors: Marc Alizon, Paris (FR); Pierre Sonigo, Paris (FR); Simon Wain-Hobson, Montigny les Bretonneux (FR); Luc Montagnier, Le Plessis Robinson (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/767,138

(22) Filed: Jan. 23, 2001

(65) Prior Publication Data

US 2002/0076691 A1    Jun. 20, 2002

Related U.S. Application Data

(60) Continuation of application No. 08/423,477, filed on Apr. 19, 1995, which is a division of application No. 07/656,796, filed on Feb. 19, 1991, now Pat. No. 5,869,631, which is a division of application No. 07/038,332, filed on Apr. 13, 1987, now Pat. No. 5,034,511.

(30) Foreign Application Priority Data

Jun. 23, 1986    (EP) .................................. 86401380

(51) Int. Cl.
*A61K 39/21* (2006.01)
(52) U.S. Cl. ................................. 424/188.1; 424/208.1
(58) Field of Classification Search ............. 424/188.1, 424/208.1
See application file for complete search history.

(56) References Cited

U.S. PATENT DOCUMENTS

| 4,784,941 A | 11/1988 | Watanabe et al. ............... 435/5 |
| 5,034,511 A | 7/1991 | Alizon et al. |
| 5,869,631 A | 2/1999 | Alizon et al. |
| 6,337,179 B1 | 1/2002 | Alizon et al. |

FOREIGN PATENT DOCUMENTS

EP    0 253 701    1/1988

OTHER PUBLICATIONS

Wang, W.-K., et al., 1995, "The highly conserved aspartic acid residue between hypervariable regions 1 and 2 of human immunodeficiency virus type 1 gp 120 is important for early stages of virus replication", J. Virol. 69(1):538-542.*

Platt, E. J., et al., 1997, "Infectious properties of human immunodeficiency virus type 1 mutants with distinct affinities for the CD4 receptor", J. Virol. 71(2):883-890.*

Chen, S. S.-L., et al., 1998, "Mutations in the leucine zipper-like heptad repeat sequence of human immunodeficiency virus type 1 gp41 dominantly interfere with wild-type virus infectivity", J. Virol. 72(6):4765-4774.*

Lee, Y.-M., et al., 1997, "Mutations in the matrix protein of human immunodeficiency virus type 1 inhibit surface expression and virion incorporation of viral envelope glycoproteins in CD4+ T lymphocytes", J. Virol. 71(2): 1443-1452.*

Neurath et al., "Radioimmunoassay and enzyme-linked immunoassay of antibodies directed against lymphadenopathy-associated virus (LAV) proteins larger than the core portein (P24)", J. Virological Methods, 12:85-92 (1985).

Wain-Hobson et al., "Nucleotide sequence of the AIDS virus, LAV", Cell, 40:9-17 (1985).

Wong-Staal et al., "Genomic diversity of human T-lymphotropic virus type III (HTLV-III)," Science, 229:759-762 (1985).

Ellrodt et al., "Isolation of Human T-lymphotropic Retrovirus (LAV) from Zairian married couple, one with AIDS, one with prodomes," The Lancet, 1383-1385 (1984).

Ratner et al., "Complete nucleotide sequence of the AIDS virus, HTLV-III," Nature, 323:277-285 (1985).

Sanchez-Pesdador et al., "Nucleotide sequence and expression of an AIDS-associated retrovirus (ARV-2)," Science 227:484-492 (1985).

Muesing et al., "Nucleic acid structure and expression of the human AIDS/lymphadenopathy retrovirus," Nature, 313: 450-458 (1985).

Alizon et al., "Molecular cloning of lymphadenopathy-associated virus," Nature, 312:757-760 (1984).

Nature, 313:277-284 (1985).

Goodenow et al., J. Acquir. Immune Defic. Syndr., 2:344-352 (1989).

Gao et al., J. Virol. 68:7433-7447 (1994).

* cited by examiner

*Primary Examiner*—Jeffrey S. Parkin
(74) *Attorney, Agent, or Firm*—Finnegan, Henderson, Farabow, Garrett & Dunner, LLP

(57) ABSTRACT

A variant of a LAV virus, designated $LAV_{ELI}$ and capable of causing AIDS. The cDNA and antigens of the $LAV_{ELI}$ virus can be used for the diagnosis of AIDS and pre-AIDS.

5 Claims, 22 Drawing Sheets

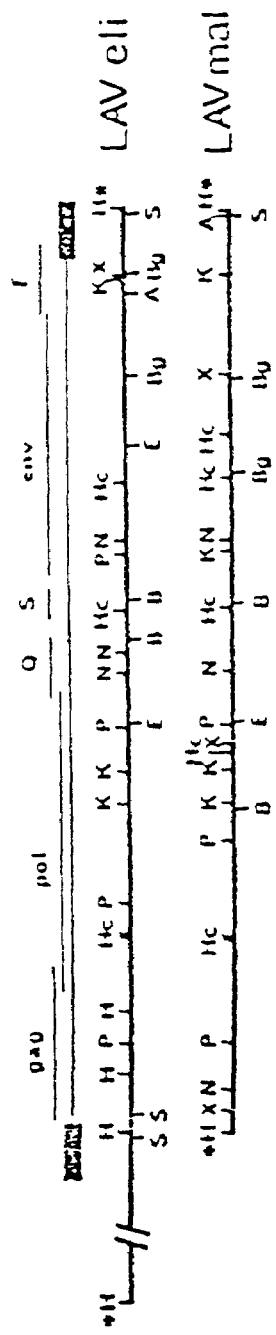
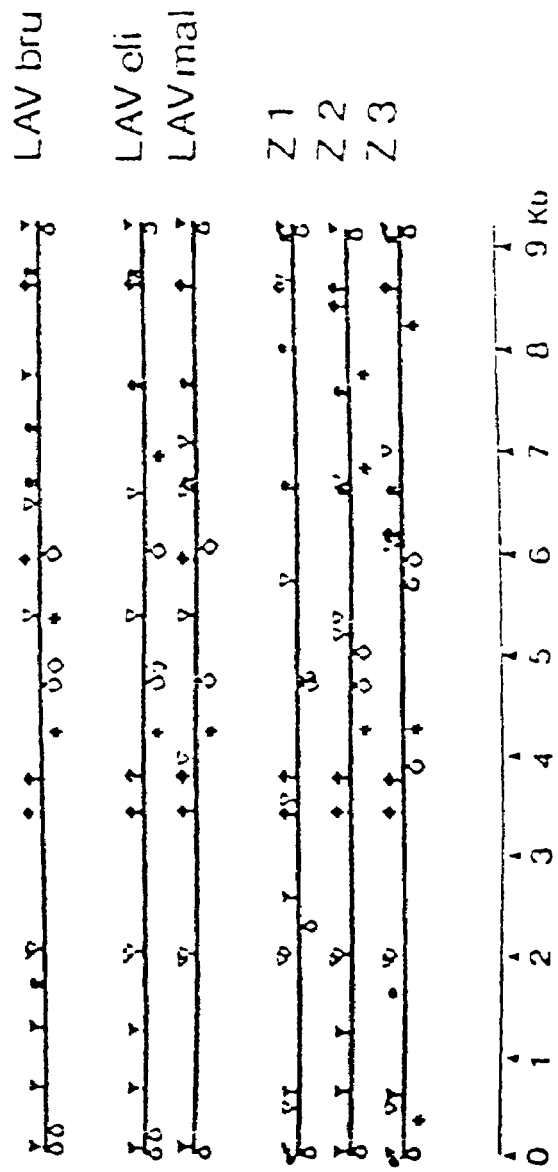
FIG. 1A
FIG. 1B

| | GAG | | POL | | ENV | | | | | |
|---|---|---|---|---|---|---|---|---|---|---|
| LAVbru vs. | | | | | Total | | OMP | | TMP | |
| HTLV-3 USA | 512 0/0 | 0.8 | 1015 0/0 | 1.3 | 856 0/0 | 1.4 | 507 5/0 | 1.6 | 349 0/0 | 1.1 |
| ARV-2 USA | 502 12/2 | 3.4 | 1003 12/0 | 3.1 | 855 17/11 | 13.0 | 505 17/10 | 14.3 | 350 0/1 | 11.2 |
| LAVeli Zaire | 500 13/1 | 9.8 | 1002 13/0 | 5.5 | 853 22/14 | 20.7 | 504 22/14 | 25.3 | 349 0/0 | 13.8 |
| LAVmal Zaire | 505 14/7 | 12.0 | 1002 13/0 | 7.7 | 859 13/11 | 21.7 | 509 13/10 | 26.4 | 350 0/1 | 14.9 |

B

| | GAG | | POL | | ENV | | | | | |
|---|---|---|---|---|---|---|---|---|---|---|
| LAVeli vs. | | | | | Total | | OMP | | TMP | |
| LAVmal | 505 1/6 | 10.8 | 1002 0/0 | 8.4 | 859 13/11 | 19.8 | 509 8/13 | 23.6 | 350 0/1 | 14.3 |

FIG. 4B

| | orf F | | central region | | | | | | |
|---|---|---|---|---|---|---|---|---|---|
| A LAVbru vs. | | | orf Q | | orf' | | orf R | | orf S |
| HTLV-3 USA | 206 / 0.0 | 1.5 | 192 / 0.0 | 0 | — | — | nd | | 80 / 0.0 | 2.5 |
| ARV-2 USA | 210 / 0.4 | 12.6 | 192 / 0.0 | 10.0 | 97 / 0.1 | | 9.4 | | 81 / 0.1 | 15.0 |
| LAVeli Zaire | 206 / 1.1 | 19.4 | 192 / 0.0 | 10.4 | 96 / 0.0 | | 11.5 | | 80 / 0.0 | 27.5 |
| LAVmal Zaire | 209 / 2.5 | 27.0 | 192 / 0.0 | 12.6 | 96 / 0.0 | | 10.4 | | 80 / 0.0 | 23.8 |
| B LAVeli vs. LAVmal | 209 / 3.6 | 22.5 | 192 / 0.0 | 12.0 | 96 / 0.0 | | 6.3 | | 80 / 0.0 | 11.3 |

LAV.ELI                        FIG. 7A

→R
GGTCTCTCTGGTTAGACCAGATTTGAGCCTGGGAGCTCTCTGGCTAGCTAGGGAACCCAC
                                    R←→.U5
TGCTTAAGCCTCAATAAAGCTTGCCTTGAGTGCTTCAAGTAGTGTGTGCCCGTCTGTTGT
                                100
GTGACTCTGGTAACTAGAGATCCCTCAGACCCCTTTAGTCAGAGTGGAAAATCTCTAGCA
U5←
GTGGCGCCCGAACAGGGACCTGAAAGCGAAAGTAGAACCAGAGGAGCTCTCTCGACGCAG
        200
GACTCGGCTTGCTGAAGCGCGCACGGCAAGAGGCGAGGGGCAGCGACTGGTGAGTACGCT
                                     →GAG        300
                                     MetGlyAlaArgAlaSerValLeuSer
AAAATTTTTGACTAGCGGAGGCTAGAAGGAGAGAGATGGGTGCGAGAGCGTCAGTATTAA

GlyGlyLysLeuAspLysTrpGluLysIleArgLeuArgProGlyGlyLysLysLysTyr
GCGGGGGAAAATTAGATAAATGGGAAAAAATTCGGTTACGGCCAGGAGGAAAGAAAAAAT
                                400
    ArgLeuLysHisIleValTrpAlaSerArgGluLeuGluArgTyrAlaLeuAsnProGly
ATAGACTAAAACATATAGTATGGGCAAGCAGGGAGCTAGAACGATATGCACTTAATCCTG

LeuLeuGluThrSerGluGlyCysLysGlnIleIleGlyGlnLeuGlnProAlaIleGln
GCCTTTTAGAAACATCAGAAGGCTGTAAACAAATAATAGGGCAGCTACAACCAGCTATTC
        500
    ThrGlyThrGluGluLeuArgSerLeuTyrAsnThrValAlaThrLeuTyrCysValHis
AGACAGGAACAGAAGAACTTAGATCATTATATAATACAGTAGCAACCCTCTATTGTGTAC
                                                        600
    LysGlyIleAspValLysAspThrLysGluAlaLeuGluLysMetGluGluGluGlnAsn
ATAAAGGAATAGATGTAAAAGACACCAAGGAAGCTTTAGAAAAGATGGAGGAAGAGCAAA

LysSerLysLysLysAlaGlnGlnAlaAlaAlaAspThrGlyAsnAsnSerGlnValSer
ACAAAAGTAAGAAAAAGGCACAGCAAGCAGCAGCTGACACAGGAAACAACAGCCAGGTCA
                                700
    GlnAsnTyrProIleValGlnAsnLeuGlnGlyGlnMetValHisGlnAlaIleSerPro
GCCAAAATTATCCTATAGTGCAGAACCTACAGGGGCAAATGGTACATCAGGCCATATCAC

ArgThrLeuAsnAlaTrpValLysValIleGluGluLysAlaPheSerProGluValIle
CTAGAACTTTGAACGCATGGGTAAAAGTAATAGAAGAAAAGGCTTTCAGCCCAGAAGTAA
                800
    ProMetPheSerAlaLeuSerGluGlyAlaThrProGlnAspLeuAsnThrMetLeuAsn
TACCCATGTTTTCAGCATTATCAGAAGGAGCCACCCCACAAGATTTAAACACCATGCTAA
                                                        900
    ThrValGlyGlyHisGlnAlaAlaMetGlnMetLeuLysGluThrIleAsnGluGluAla
ACACAGTGGGGGGACATCAAGCAGCCATGCAAATGCTAAAAGAGACCATCAATGAGGAAG

AlaGluTrpAspArgLeuHisProValHisAlaGlyProIleAlaProGlyGlnMetArg
CTGCAGAATGGGATAGGTTACATCCAGTGCATGCAGGGCCTATTGCACCAGGCCAGATGA
                                1000
    GluProArgGlySerAspIleAlaGlyThrThrSerThrLeuGlnGluGlnIleAlaTrp
GAGAACCAAGGGGAAGTGATATAGCAGGAACTACTAGTACCCTTCAGGAACAAATAGCAT

MetThrSerAsnProProIleProValGlyGluIleTyrLysArgTrpIleIleValGly
GGATGACAAGTAACCCACCTATCCCAGTAGGAGAAATCTATAAAAGATGGATAATTGTGG
                1100
    LeuAsnLysIleValArgMetTyrSerProValSerIleLeuAspIleArgGlnGlyPro
GATTAAATAAAATAGTAAGAATGTATAGCCCTGTCAGCATTTTGGACATAAGACAGGGAC
                                                        1200

FIG. 7B

```
    LysGluProPheArgAspTyrValAspArgPheTyrLysThrLeuArgAlaGluGlnAla
    CAAAGGAACCTTTTAGAGACTATGTAGACCGGTTCTATAAAACTCTAAGAGCCGAGCAAG
       •           •           •           •           •           •
    SerGlnAspValLysAsnTrpMetThrGluThrLeuLeuValGlnAsnAlaAsnProAsp
    CTTCACAGGATGTAAAAAATTGGATGACAGAAACCTTGTTGGTCCAAAATGCAAACCCAG
                   •         1300        •           •           •
    CysLysThrIleLeuLysAlaLeuGlyProGlnAlaThrLeuGluGluMetMetThrAla
    ATTGCAAGACTATCTTAAAAGCATTGGGACCACAGGCTACACTAGAAGAAATGATGACAG
       •           •           •           •           •           •
    CysGlnGlyValGlyGlyProSerHisLysAlaArgValLeuAlaGluAlaMetSerGln
    CATGTCAGGGAGTGGGGGGGCCCAGCCATAAAGCAAGAGTTCTGGCTGAGGCAATGAGCC
                 1400          •           •           •           •
    AlaThrAsnSerValThrThrAlaMetMetGlnArgGlyAsnPheLysGlyProArgLys
    AAGCAACAAATTCAGTTACTACAGCAATGATGCAGAGAGGCAATTTTAAGGGCCCAAGAA
       •           •           •           •         1500          •
    IleIleLysCysPheAsnCysGlyLysGluGlyHisIleAlaLysAsnCysArgAlaPro
    AAATTATTAAGTGTTTCAATTGTGGCAAAGAAGGGCACATAGCAAAAAATTGCAGGGCCC
       •           •           •           •           •           •
    ArgLysLysGlyCysTrpArgCysGlyLysGluGlyHisGlnLeuLysAspCysThrGlu
    CTAGGAAAAAGGGCTGTTGGAGATGTGGAAAGGAAGGACACCAACTAAAAGATTGCACTG
       •      ⤳POL •         1600        •           •           •
          PhePheArgGluAsnLeuAlaPheProGlnGlyLysAlaGlyGluLeu
    ArgGlnAlaAsnPheLeuGlyArgIleTrpProSerHisLysGlyArgProGlyAsnPhe
    AGAGACAGGCTAATTTTTTAGGGAGAATTTGGCCTTCCCACAAGGGAAGGCCGGGGAACT
       •           •           •           •           •           •
    SerProLysGlnThrArgAlaAsnSerProThrSerArgGluLeuArgValTrpGlyArg
    LeuGlnSerArgProGluProThrAlaProProAlaGluSerPheGlyPheGlyGluGlu
    TTCTCCAAAGCAGACCAGAGCCAACAGCCCCACCAGCAGAGAGCTTCGGGTTTGGGGAAG
                 1700          •           •           •           •
    AspAsnProLeuSerLysThrGlyAlaGluArgGlnGlyThrValSerPheAsnPhePro
    IleThrProSerGlnLysGlnGluGlnLysAspLysGluLeuTyrProLeuThrSerLeu
    AGATAACCCCCTCTCAAAAACAGGAGCAGAAAGACAAGGAACTGTATCCTTTAACTTCCC
       •           •           •   •GAG⤶  •           •         1800
    GlnIleThrLeuTrpGlnArgProLeuValAlaIleLysIleGlyGlyGlnLeuLysGlu
    LysSerLeuPheGlyAsnAspProLeuSerGln|
    TCAAATCACTCTTTGGCAACGACCCCTTGTCGCAATAAAAATAGGGGACAGCTAAAGGA
       •           •           •           •           •           •
    AlaLeuLeuAspThrGlyAlaAspAspThrValLeuGluGluMetAsnLeuProGlyLys
    AGCTCTATTAGATACAGGAGCAGATGATACAGTATTAGAAGAAATGAATTTGCCAGGAAA
       •           •           •         1900        •           •
    TrpLysProLysMetIleGlyGlyIleGlyGlyPheIleLysValArgGlnTyrAspGln
    ATGGAAACCAAAAATGATAGGGGGAATTGGAGGTTTTATCAAAGTAAGACAGTATGATCA
       •           •           •           •           •           •
    IleProIleGluIleCysGlyGlnLysAlaIleGlyThrValLeuValGlyProThrPro
    AATACCCATAGAAATCTGTGGACAGAAAGCTATAGGTACAGTATTAGTAGGACCTACGCC
                 2000          •           •           •           •
    ValAsnIleIleGlyArgAsnLeuLeuThrGlnIleGlyCysThrLeuAsnPheProIle
    TGTCAACATAATCGGAAGAAATTTGTTGACCCAGATTGGCTGCACTTTAAATTTTCCAAT
       •           •           •           •           •         2100
    SerProIleGluThrValProValLysLeuLysProGlyMetAspGlyProLysValLys
    TAGTCCTATTGAAACTGTACCAGTAAAATTAAAGCCAGGAATGGATGGCCCAAAAGTTAA
       •           •           •           •           •           •
    GlnTrpProLeuThrGluGluLysIleLysAlaLeuThrGluIleCysThrAspMetGlu
    ACAATGGCCATTGACAGAAGAAAAAATAAAAGCATTAACAGAAATTTGTACAGATATGGA
       •           •           •         2200        •           •
```

FIG. 7C

```
LysGluGlyLysIleSerArgIleGlyProGluAsnProTyrAsnThrProIlePheAla
AAAGGAAGGAAAAATTTCAAGAATTGGGCCTGAAAATCCATACAATACTCCAATATTTGC
                .         .         .         .         .         .
IleLysLysLysAspSerThrLysTrpArgLysLeuValAspPheArgGluLeuAsnLys
CATAAAGAAAAAAGACAGTACCAAGTGGAGAAAATTAGTAGATTTCAGAGAACTTAATAA
                .         2300      .         .         .         .
ArgThrGlnAspPheTrpGluValGlnLeuGlyIleProHisProAlaGlyLeuLysLys
GAGAACTCAAGATTTCTGGGAAGTTCAATTAGGAATACCGCATCCTGCAGGGCTGAAAAA
                .         .         .         .         2400
LysLysSerValThrValLeuAspValGlyAspAlaTyrPheSerValProLeuAspGlu
GAAAAAATCAGTAACAGTACTGGATGTGGGTGATGCATATTTTCAGTTCCCTTAGATGA
                .         .         .         .         .         .
AspPheArgLysTyrThrAlaPheThrIleSerSerIleAsnAsnGluThrProGlyIle
AGATTTTAGGAAATATACCGCCTTTACCATATCTAGTATAAACAATGAGACACCAGGGAT
                .         .         2500      .         .         .
ArgTyrGlnTyrAsnValLeuProGlnGlyTrpLysGlySerProAlaIlePheGlnSer
TAGATATCAGTACAATGTGCTTCCACAGGGATGGAAAGGATCACCGGCAATATTCCAAAG
                .         .         .         .         .         .
SerMetThrLysIleLeuGluProPheArgLysGlnAsnProGluMetValIleTyrGln
TAGCATGACAAAAATCTTAGAGCCCTTTAGAAAACAAAATCCAGAAATGGTTATCTATCA
                .         2600      .         .         .         .
TyrMetAspAspLeuTyrValGlySerAspLeuGluIleGlyGlnHisArgThrLysIle
ATACATGGATGATTTGTATGTAGGATCTGACTTAGAAATAGGGCAGCATAGGACAAAAAT
                .         .         .         .         .         2700
GluLysLeuArgGluHisLeuLeuArgTrpGlyPheThrArgProAspLysLysHisGln
AGAGAAATTAAGAGAACATCTATTGAGGTGGGGATTTACCAGACCAGATAAAAAACATCA
                .         .         .         .         .         .
LysGluProProPheLeuTrpMetGlyTyrGluLeuHisProAspLysTrpThrValGln
GAAAGAACCCCCATTTCTTTGGATGGGTTATGAACTCCATCCTGATAAATGGACAGTACA
                .         .         .         2800      .         .
SerIleLysLeuProGluLysGluSerTrpThrValAsnAspIleGlnAsnLeuValGlu
GTCTATAAAACTGCCAGAAAAGGAGAGCTGGACTGTCAATGATATACAGAACTTAGTGGA
                .         .         .         .         .         .
ArgLeuAsnTrpAlaSerGlnIleTyrProGlyIleLysValArgGlnLeuCysLysLeu
GAGATTAAACTGGGCAAGCCAGATTTATCCAGGAATTAAAGTAAGACAATTATGTAAACT
                .         2900      .         .         .         .
LeuArgGlyThrLysAlaLeuThrGluValIleProLeuThrGluGluAlaGluLeuGlu
CCTTAGGGGAACCAAAGCACTAACAGAAGTAATACCACTAACAGAAGAAGCAGAATTAGA
                .         .         .         .         .         3000
LeuAlaGluAsnArgGluIleLeuLysGluProValHisGlyValTyrTyrAspProSer
ACTGGCAGAAAACAGGGAAATTTTAAAAGAACCAGTACATGGAGTGTATTATGACCCATC
                .         .         .         .         .         .
LysAspLeuIleAlaGluIleGlnLysGlnGlyHisGlyGlnTrpThrTyrGlnIleTyr
AAAAGACTTAATAGCAGAAATACAGAAACAAGGGCACGGCCAATGGACATACCAAATTTA
                .         .         .         3100      .         .
GlnGluProPheLysAsnLeuLysThrGlyLysTyrAlaArgMetArgGlyAlaHisThr
TCAAGAACCATTTAAAAATCTGAAAACAGGAAAGTATGCAAGAATGAGGGGTGCCCACAC
                .         .         .         .         .         .
AsnAspValLysGlnLeuAlaGluAlaValGlnArgIleSerThrGluSerIleValIle
TAATGATGTAAAGCAATTAGCAGAGGCAGTGCAAAGAATATCCACAGAAAGCATAGTGAT
                .         .         3200      .         .         .
TrpGlyArgThrProLysPheArgLeuProIleGlnLysGluThrTrpGluThrTrpTrp
ATGGGGAAGGACTCCTAAATTTAGACTACCCATACAAAAGGAAACATGGGAAACATGGTG
                .         .         .         .         .         3300
```

FIG. 7D

```
AlaGluTyrTrpGlnAlaThrTrpIleProGluTrpGluPheValAsnThrProProLeu
GGCAGAGTATTGGCAAGCCACTTGGATTCCTGAGTGGGAATTTGTCAATACCCCTCCTTT

ValLysLeuTrpTyrGlnLeuGluLysGluProIleIleGlyAlaGluThrPheTyrVal
AGTAAAATTATGGTACCAGTTAGAGAAGGAACCCATAATAGGAGCAGAAACTTTCTATGT
                                  3400
AspGlyAlaAlaAsnArgGluThrLysLeuGlyLysAlaGlyTyrValThrAspArgGly
AGATGGGGCAGCTAATAGAGAGACTAAATTAGGAAAAGCAGGATATGTTACTGACAGAGG

ArgGlnLysValValProLeuThrAspThrThrAsnGlnLysThrGluLeuGlnAlaIle
AAGACAGAAAGTTGTCCCTTTGACTGACACGACAAATCAGAAGACTGAGTTACAAGCAAT
                  3500
AsnLeuAlaLeuGlnAspSerGlyLeuGluValAsnIleValThrAspSerGlnTyrAla
TAATCTAGCCTTGCAGGATTCGGGATTAGAAGTAAACATAGTAACAGATTCACAATATGC
                                              3600
LeuGlyIleIleGlnAlaGlnProAspLysSerGluSerGluLeuValAsnGlnIleIle
ATTAGGAATCATTCAAGCACAACCAGATAAGAGTGAATCAGAGTTAGTCAATCAAATAAT

GluGlnLeuIleLysLysGluLysValTyrLeuAlaTrpValProAlaHisLysGlyIle
AGAGCAGTTAATAAAAAAGGAAAAGGTTTACCTGGCATGGGTACCAGCACACAAAGGAAT
                                  3700
GlyGlyAsnGluGlnValAspLysLeuValSerGlnGlyIleArgLysValLeuPheLeu
TGGAGGAAATGAACAAGTAGATAAATTAGTCAGTCAAGGAATCAGGAAAGTACTATTTTT

AspGlyIleAspLysAlaGlnGluGluHisGluLysTyrHisAsnAsnTrpArgAlaMet
GGATGGAATAGATAAGGCTCAAGAAGAACATGAGAAATATCACAACAATTGGAGAGCAAT
                  3800
AlaSerAspPheAsnLeuProProValValAlaLysGluIleValAlaSerCysAspLys
GGCTAGTGATTTTAACCTACCACCCGTGGTAGCAAAAGAAATAGTAGCTAGCTGTGATAA
                                              3900
CysGlnLeuLysGlyGluAlaMetHisGlyGlnValAspCysSerProGlyIleTrpGln
ATGTCAGCTAAAAGGAGAAGCCATGCATGGACAAGTAGACTGTAGTCCAGGAATATGGCA

LeuAspCysThrHisLeuGluGlyLysValIleLeuValAlaValHisValAlaSerGly
ATTAGATTGTACACACTTAGAAGGAAAAGTTATCCTGGTAGCAGTTCATGTAGCCAGTGG
                              4000
TyrIleGluAlaGluValIleProAlaGluThrGlyGlnGluThrAlaTyrPheLeuLeu
CTATATAGAAGCAGAAGTTATTCCAGCAGAAACAGGGCAGGAAACAGCATATTTTCTTTT

LysLeuAlaGlyArgTrpProValLysValValHisThrAspAsnGlySerAsnPheThr
AAAATTAGCAGGAAGATGGCCAGTAAAAGTAGTACATACAGACAATGGCAGCAATTTCAC
                  4100
SerAlaAlaValLysAlaAlaCysTrpTrpAlaGlyIleLysGlnGluPheGlyIlePro
CAGTGCTGCAGTTAAGGCCGCCTGTTGGTGGGCAGGTATCAAACAGGAATTTGGAATTCC
                                        4200
TyrAsnProGlnSerGlnGlyValValGluSerMetAsnLysGluLeuLysLysIleIle
CTACAATCCCCAAAGTCAAGGAGTAGTAGAATCTATGAATAAAGAATTAAAGAAAATTAT

GlyGlnValArgAspGlnAlaGluHisLeuLysThrAlaValGlnMetAlaValPheIle
AGGACAGGTAAGAGATCAAGCTGAACATCTTAAGACAGCAGTACAAATGGCAGTATTCAT
                              4300
HisAsnPheLysArgArgArgGlyIleGlyGlyTyrSerAlaGlyGluArgIleIleAsp
CCACAATTTTAAAAGAAGAAGGGGGATTGGGGGATACAGTGCAGGGGAAAGAATAATAGA
```

FIG. 7E

```
        IleIleAlaThrAspIleGlnThrLysGluLeuGlnLysGlnIleIleLysIleGlnAsn
        CATAATAGCAACAGACATACAAACTAAAGAATTACAAAAACAAATTATAAAAATTCAAAA-
                       4400        .        .        .        .
        PheArgValTyrTyrArgAspSerArgAspProIleTrpLysGlyProAlaLysLeuLeu
        TTTTCGGGTTTATTACAGAGACAGCAGAGATCCAATTTGGAAAGGACCAGCAAAGCTCCT
           .        .        .        .        .        4500
        TrpLysGlyGluGlyAlaValValIleGlnAspLysSerAspIleLysValValProArg
        CTGGAAAGGTGAAGGGGCAGTAGTAATACAAGACAAGAGTGACATAAAGGTAGTACCAAG
           .        .        .  ┌─Q  .        .        .
        ArgLysValLysIleIleArgAsp TyrGlyLysGlnMetAlaGlyAspAspCysValAla
                                │MetGluAsnArgTrpGlnValMetIleValTrpGln
        AAGAAAAGTAAAGATTATTAGGGATTATGGAAAACAGATGGCAGGTGATGATTGTGTGGC
           .     POL←┐.        .        4600     .        .
        SerArgGlnAspGluAsp│
        ValAspArgMetArgIle│LysThrTrpLysSerLeuValLysHisHisMetTyrValSer
        AAGTAGACAGGATGAGGAT│AAAACATGGAAAAGTTTAGTAAAACACCATATGTATGTTT
           .        .        .        .        .        .
        LysLysAlaAsnArgTrpPheTyrArgHisHisTyrGluSerProHisProLysIleSer
        CAAAGAAAGCTAACAGATGGTTTATAGACATCACTATGAAAGCCCCCACCCAAAAATAA
           .        .        4700     .        .        .
        SerGluValHisIleProLeuGlyGluAlaArgLeuValIleLysThrTyrTrpGlyLeu
        GTTCAGAAGTACACATCCCACTAGGAGAAGCTAGACTGGTAATAAAAACATATTGGGGTC
           .        .        .        .        .        4800
        HisThrGlyGluArgGluTrpHisLeuGlyGlnGlyValSerIleGluTrpArgLysArg
        TGCATACAGGAGAAAGAGAATGGCATCTGGGTCAGGGAGTCTCCATAGAATGGAGGAAAA
           .        .        .        .        .        .
        ArgTyrSerThrGlnValAspProGlyLeuAlaAspGlnLeuIleHisMetTyrTyrPhe
        GGAGATATAGCACACAAGTAGACCCTGGCCTGGCAGACCAACTAATTCATATGTATTATT
           .        .        .        .        4900     .        .
        AspCysPheSerGluSerAlaIleArgLysAlaIleLeuGlyAspIleValSerProArg
        TTGATTGTTTTTCAGAATCTGCTATAAGAAAAGCCATATTAGGAGATATAGTTAGTCCTA
           .        .        .        .        .        .
        CysGluTyrGlnAlaGlyHisAsnLysValGlySerLeuGlnTyrLeuAlaLeuThrAla
        GGTGTGAGTATCAAGCAGGACATAACAAGGTAGGATCCCTACAGTATTTGGCACTAACAG
           .        5000     .        .        .        .
        LeuIleAlaProLysGlnIleLysProProLeuProSerValArgLysLeuThrGluAsp
        CATTAATAGCACCAAAACAGATAAAGCCACCTTTGCCTAGTGTTAGGAAGCTAACAGAAG
           ┌─>.R  .        .        .        .        5100
           │MetGluGlnAlaProAlaAspGlnGlyProGlnArgGluProTyrAsnGluTrpAla
           Arg│TrpAsnLysProGlnGlnThrArgGlyHisArgGlySerHisThrMetAsnGlyHis
        ATAG│ATGGAACAAGCCCCAGCAGACCAGGGGCCACAGAGGGAGCCATACAATGAATGGGC
        Q←┐  │
          │LeuGluLeuLeuGluGluLeuLysSerGluAlaValArgHisPheProArgIleTrpLeu
        AT│TAGAGCTTTTAGAGGAGCTTAAGAGTGAAGCTGTTAGACATTTTCCTAGGATATGGCT
           .        .        .        5200     .        .
        HisSerLeuGlyGlnHisIleTyrGluThrTyrGlyAspThrTrpValGlyValGluAla
        CCATAGCTTAGGACAACATATTTATGAAACTTATGGGGATACCTGGGTAGGAGTTGAAGC
           .        .        .        .        .        .
        IleIleArgIleLeuGlnGlnLeuLeuPheIleHisPheArgIleGlyCysGlnHisSer
        TATAATAAGAATACTGCAACAATTACTGTTTATTCATTTCAGAATTGGGTGTCAACATAG
           .        5300     .        ┌─>S  .   R ←┐  .
        ArgIleGlyIleIleArgGlnArgArgAlaArg│AsnGlySerSerArgSer│
                                          │MetAspProValAspPro│AsnLeuGlu
        CAGAATAGGCATTATTCGACAGAGAAGAGCAAGA│ATGGATCCAGTAGATCC│TAACCTAG
           .        .        .        .   │    .        .   │    5400
```

FIG. 7F

```
ProTrpAsnHisProGlySerGlnProArgThrProCysAsnLysCysHisCysLysLys
AGCCCTGGAACCATCCAGGAAGTCAGCCTAGGACTCCTTGTAACAAGTGTCATTGTAAAA
                    .              .              .              .
   CysCysTyrHisCysProValCysPheLeuAsnLysGlyLeuGlyIleSerTyrGlyArg
AGTGTTGCTATCATTGCCCAGTTTGCTTCTTAAACAAAGGCTTAGGCATCTCCTATGGCA
                                      5500                  .
   LysLysArgArgGlnArgArgGlyProProGlnGlyGlyGlnAlaHisGlnValProIle
GGAAGAAGCGGAGACAGCGACGAGGACCTCCTCAAGGCGGTCAGGCTCATCAAGTTCCTA
         S←┐
   ProLysGln│
TACCAAAGCAG TAAGTAGTACATGTAATGCAACCTTTAGGGATAATAGCAATAGCAGCAT
                    5600           .              .              .
TAGTAGTAGCAATAATACTAGCAATAGTTGTGTGGACCATAGTATTCATAGAATATAGAA
                    .              .              .        5700
GGATAAAAAAGCAAAGGAGAATAGACTGTTTACTTGATAGAATAACAGAAAGAGCAGAAG
         ┌→ENV         .              .              .              .
         │MetArgAlaArgGlyIleGluArgAsnCysGlnAsnTrpTrpLysTrpGly
ACAGTGGCAATGAGAGCGAGGGGGATAGAGAGAAATTGTCAAAACTGGTGGAAATGGGGC
                    .              .    5800                     .
   IleMetLeuLeuGlyIleLeuMetThrCysSerAlaAlaAspAsnLeuTrpValThrVal
ATCATGCTCCTTGGGATATTGATGACCTGTAGTGCTGCAGACAATCTGTGGGTCACAGTT
                    .              .              .              .
   TyrTyrGlyValProValTrpLysGluAlaThrThrThrLeuPheCysAlaSerAspAla
TATTATGGGGTGCCTGTATGGAAGGAAGCAACCACCACTCTATTTTGTGCATCAGATGCT
                5900                  .              .              .
   LysSerTyrGluThrGluAlaHisAsnIleTrpAlaThrHisAlaCysValProThrAsp
AAATCATATGAAACAGAGGCACATAATATCTGGGCCACACATGCCTGTGTACCCACGGAC
                    .              .              .         6000
   ProAsnProGlnGluIleAlaLeuGluAsnValThrGluAsnPheAsnMetTrpLysAsn
CCCAACCCACAAGAAATAGCACTGGAAAATGTGACAGAAAACTTTAACATGTGGAAAAAT
                    .              .              .              .
   AsnMetValGluGlnMetHisGluAspIleIleSerLeuTrpAspGlnSerLeuLysPro
AACATGGTGGAACAGATGCATGAGGATATAATCAGTTTATGGGATCAAAGCCTAAAACCA
                    .         6100                  .              .
   CysValLysLeuThrProLeuCysValThrLeuAsnCysSerAspGluLeuArgAsnAsn
TGTGTAAAATTAACCCCACTCTGTGTCACTTTAAACTGTAGTGATGAATTGAGGAACAAT
               - - - -               .              .              .
   GlyThrMetGlyAsnAsnValThrThrGluGluLysGlyMetLysAsnCysSerPheAsn
GGCACTATGGGGAACAATGTCACTACAGAGGAGAAAGGAATGAAAAACTGCTCTTTCAAT
                    .    6200                     .              .
   ValThrThrValLeuLysAspLysLysGlnGlnValTyrAlaLeuPheTyrArgLeuAsp
GTAACCACAGTACTAAAAGATAAGAAGCAGCAAGTATATGCACTTTTTTATAGACTTGAT
                    .              .              .         6300
   IleValProIleAspAsnAspSerSerThrAsnSerThrAsnTyrArgLeuIleAsnCys
ATAGTACCAATAGACAATGATAGTAGTACCAATAGTACCAATTATAGGTTAATAAATTGT
                    .              .              .              .
   AsnThrSerAlaIleThrGlnAlaCysProLysValSerPheGluProIleProIleHis
AATACCTCAGCCATTACACAGGCTTGTCCAAAGGTATCCTTTGAGCCAATTCCCATACAT
                    .         6400                  .              .
   TyrCysAlaProAlaGlyPheAlaIleLeuLysCysArgAspLysLysPheAsnGlyThr
TATTGTGCCCCAGCTGGTTTTGCGATTCTAAAGTGTAGAGATAAGAAGTTCAATGGAACA
                    .              .              .              .
   GlyProCysThrAsnValSerThrValGlnCysThrHisGlyIleArgProValValSer
GGCCCATGCACAAATGTCAGCACAGTACAATGTACACATGGAATTAGGCCAGTGGTGTCA
                6500                  .              .              .
```

FIG. 7G

```
ThrGlnLeuLeuLeuAsnGlySerLeuAlaGluGluGluValIleIleArgSerGluAsn
ACTCAACTGCTGTTGAATGGCAGTCTAGCAGAAGAAGAGGTCATAATTAGATCCGAAAAT
                    .              .              .              .              6600
LeuThrAsnAsnAlaLysAsnIleIleAlaHisLeuAsnGluSerValLysIleThrCys
CTCACAAACAATGCTAAAAACATAATAGCACATCTTAATGAATCTGTAAAAATTACCTGT
     .              .              .              .              .
AlaArgProTyrGlnAsnThrArgGlnArgThrProIleGlyLeuGlyGlnSerLeuTyr
GCAAGGCCCTATCAAAATACAAGACAAAGAACACCTATAGGACTAGGGCAATCACTCTAT
                    .              .              6700           .              .
ThrThrArgSerArgSerIleIleGlyGlnAlaHisCysAsnIleSerArgAlaGlnTrp
ACTACAAGATCAAGATCAATAATAGGACAAGCACATTGTAATATTAGTAGAGCACAATGG
          .              .              .              .              .
SerLysThrLeuGlnGlnValAlaArgLysLeuGlyThrLeuLeuAsnLysThrIleIle
AGTAAAACTTTACAACAAGTAGCTAGAAAATTAGGAACCCTTCTTAACAAAACAATAATA
                    6800           .              .              .              .
LysPheLysProSerSerGlyGlyAspProGluIleThrThrHisSerPheAsnCysGly
AAGTTTAAACCATCCTCAGGAGGGGACCCAGAAATTACAACACACAGTTTTAATTGTGGA
                    .              .              .              .              6900
GlyGluPhePheTyrCysAsnThrSerGlyLeuPheAsnSerThrTrpAsnIleSerAla
GGGGAATTCTTCTACTGTAATACATCAGGACTGTTTAATAGTACATGGAATATTAGTGCA
     .              .              .              .              .
TrpAsnAsnIleThrGluSerAsnAsnSerThrAsnThrAsnIleThrLeuGlnCysArg
TGGAATAATATTACAGAGTCAAATAATAGCACAAACACAAACATCACACTCCAATGCAGA
                    .              .              7000           -              -
IleLysGlnIleIleLysMetValAlaGlyArgLysAlaIleTyrAlaProProIleGlu
ATAAAACAAATTATAAAGATGGTGGCAGGCAGGAAAGCAATATATGCCCCTCCTATCGAA
          .              .              .              .              .
ArgAsnIleLeuCysSerSerAsnIleThrGlyLeuLeuLeuThrArgAspGlyGlyIle
AGAAACATTCTATGTTCATCAAATATTACAGGGCTACTATTGACAAGAGATGGTGGTATA
                    7100           .              .              .              .
AsnAsnSerThrAsnGluThrPheArgProGlyGlyGlyAspMetArgAspAsnTrpArg
AATAATAGTACTAACGAGACCTTTAGACCTGGAGGAGGAGATATGAGGGACAATTGGAGA
                    .              .              .              .              7200
SerGluLeuTyrLysTyrLysValValGlnIleGluProLeuGlyValAlaProThrArg
AGTGAATTATATAAATATAAGGTAGTACAAATTGAACCACTAGGAGTAGCACCCACCAGG
     .              .              .              .              .
AlaLysArgArgValValGluArgGluLysArgAlaIleGlyLeuGlyAlaMetPheLeu
GCAAAGAGAAGAGTGGTGGAAAGAGAAAAAAGAGCAATAGGATTAGGAGCTATGTTCCTT
                    .              .              7300           .              .
GlyPheLeuGlyAlaAlaGlySerThrMetGlyAlaArgSerValThrLeuThrValGln
GGGTTCTTGGGAGCAGCAGGAAGCACGATGGGCGCACGGTCAGTGACGCTGACGGTACAG
     .              .              .              .              .
AlaArgGlnLeuMetSerGlyIleValGlnGlnGlnAsnAsnLeuLeuArgAlaIleGlu
GCCAGACAATTAATGTCTGGTATAGTGCAACAGCAAAACAATTTGCTGAGGGCTATAGAG
                    7400           .              .              .              .
AlaGlnGlnHisLeuLeuGlnLeuThrValTrpGlyIleLysGlnLeuGlnAlaArgIle
GCGCAACAGCATCTGTTGCAACTCACGGTCTGGGGCATTAAACAGCTCCAGGCAAGAATC
                    .              .              .              .              7500
LeuAlaValGluArgTyrLeuLysAspGlnGlnLeuLeuGlyIleTrpGlyCysSerGly
CTGGCTGTGGAAAGATACCTAAAGGATCAACAGCTCCTAGGAATTTGGGGTTGCTCTGGA
     .              .              .              .              .
```

FIG. 7H

```
LysHisIleCysThrThrAsnValProTrpAsnSerSerTrpSerAsnArgSerLeuAsn
AAACACATTTGCACCACTAATGTGCCCTGGAACTCTAGTTGGAGTAATAGATCTCTAAAT
                              7600
GluIleTrpGlnAsnMetThrTrpMetGluTrpGluArgGluIleAspAsnTyrThrGly
GAGATTTGGCAGAACATGACCTGGATGGAGTGGAAAGAGAAATTGACAATTACACAGGC

LeuIleTyrSerLeuIleGluGluSerGlnThrGlnGlnGluLysAsnGluLysGluLeu
TTAATATATAGCTTAATTGAGGAATCGCAGACCCAGCAAGAAAAGAATGAAAAGAATTG
                7700
LeuGluLeuAspLysTrpAlaSerLeuTrpAsnTrpPheSerIleThrGlnTrpLeuTrp
TTGGAATTGGACAAGTGGGCAAGTTTGTGGAATTGGTTTAGCATAACACAATGGCTGTGG
                                           7800
TyrIleLysIlePheIleMetIleIleGlyGlyLeuIleGlyLeuArgIleValPheAla
TATATAAAAATATTCATAATGATAATAGGAGGCTTGATAGGTTTAAGAATAGTTTTTGCT

ValLeuSerLeuValAsnArgValArgGlnGlyTyrSerProLeuSerPheGlnThrLeu
GTGCTTTCTTTAGTAAATAGAGTTAGGCAGGGATACTCACCTCTGTCGTTTCAGACCCTC
                     7900
LeuProAlaProArgGlyProAspArgProGluGlyThrGluGluGluGlyGlyGluArg
CTCCCAGCCCCGAGGGGACCCGACAGGCCCGAAGGAACAGAAGAAGAAGGTGGAGAGCGA

GlyArgAspArgSerValArgLeuLeuAsnGlyPheSerAlaLeuIleTrpAspAspLeu
GGCAGAGACAGATCCGTGAGATTGCTGAACGGATTCTCGGCACTTATCTGGGACGACCTG
            8000
ArgSerLeuCysLeuPheSerTyrHisArgLeuArgAspLeuIleLeuIleAlaValArg
CGGAGCCTGTGCCTCTTCAGCTACCACCGCTTGAGAGACTTAATCTTAATTGCAGTGAGG
                                             8100
IleValGluLeuLeuGlyArgArgGlyTrpAspIleLeuLysTyrLeuTrpAsnLeuLeu
ATTGTAGAACTTCTGGGACGCAGGGGGTGGGACATCCTCAAATATCTGTGGAATCTCCTA

GlnTyrTrpSerGlnGluLeuArgAsnSerAlaSerSerLeuPheAspAlaIleAlaIle
CAGTATTGGAGTCAGGAACTGAGGAACAGTGCTAGTAGCTTGTTTGATGCCATAGCAATA
                     8200
AlaValAlaGluGlyThrAspArgValIleGluIleIleGlnArgAlaCysArgAlaVal
GCAGTAGCTGAGGGGACAGATAGAGTTATAGAAATAATACAAAGAGCTTGCAGAGCTGTT
                                                    W
LeuAsnIleProArgArgIleArgGlnGlyLeuGluArgSerLeuLeu      F
CTTAACATACCCAGAAGAATAAGACAGGGCTTAGAAAGGTCTTTACTTTAAAATGGGTGG   MetGlyGly
                 8300
 LysTrpSerLysSerSerIleValGlyTrpProAlaIleArgGluArgIleArgArgThr
 CAAATGGTCAAAAAGTAGTATAGTGGGATGGCCTGCTATAAGGGAAAGAATAAGAAGAAC
                                                      8400
 AsnProAlaAlaAspGlyValGlyAlaValSerArgAspLeuGluLysHisGlyAlaIle
 TAATCCAGCAGCAGATGGGGTAGGAGCAGTATCTCGAGACCTGGAAAAACATGGGGCAAT

ThrSerSerAsnThrAlaSerThrAsnAlaAspCysAlaTrpLeuGluAlaGlnGluGlu
   CACAAGTAGCAATACAGCAAGTACTAATGCTGACTGTGCCTGGCTAGAAGCACAAGAAGA
                           8500
  SerAspGluValGlyPheProValArgProGlnValProLeuArgProMetThrTyrLys
  GAGCGACGAGGTGGGCTTTCCAGTCAGACCCCAGGTACCTTTAAGACCAATGACTTACAA
                                      U3
  GluAlaLeuAspLeuSerHisPheLeuLysGluLysGlyGlyLeuGluGlyLeuIleTrp
  AGAAGCTCTAGATCTCAGCCACTTTTTAAAAGAAAAGGGGGACTGGAAGGGCTAATTTG
                 8600
```

FIG. 7I

```
        SerLysLysArgGlnGluIleLeuAspLeuTrpValTyrAsnThrGlnGlyIlePhePro
        GTCCAAAAAGAGACAAGAGATCCTTGATCTTTGGGTCTACAACACACAAGGCATCTTCCC
                  .         .         .         .         .
                                                                    8700
        AspTrpGlnAsnTyrThrProGlyProGlyIleArgTyrProLeuThrPheGlyTrpCys
        TGATTGGCAAAACTACACACCAGGGCCAGGGATCAGATATCCACTAACCTTTGGATGGTG
                  .         .         .         .         .
        TyrGluLeuValProValAspProGlnGluValGluGluAspThrGluGlyGluThrAsn
        CTACGAGCTAGTACCAGTTGATCCACAGGAGGTAGAAGAAGACACTGAAGGAGAGACCAA
                  .         .         8800
        SerLeuLeuHisProIleCysGlnHisGlyMetGluAspProGluArgGlnValLeuLys
        CAGCTTGTTACACCCTATATGCCAGCATGGAATGGAGGACCCGGAGAGACAAGTGTTAAA
                  .         .         .         .         .
        TrpArgPheAsnSerArgLeuAlaPheGluHisLysAlaArgGluMetHisProGluPhe
        ATGGAGATTTAACAGCAGACTAGCATTTGAGCACAAGGCCCGAGAGATGCATCCGGAGTT
                  .         8900      .         .         .         .
        TyrLysAsn
        CTACAAAAACTGATGACACCGAGCTTTCTACAAGGGACTTTCCGCTGGGGACTTTCCAGG
                  .         .         .         .         .
                                                                    9000
        GAGGCGTGGACTGGGCGGGACTGGGGAGTGGCTAACCCTCAGATGCTGCATATAAGCAGC
                  .         U3 ← → R   .         .         .         .
        TGCTTTTTGCCTGTACTGGGTCTCTCTGGTTAGACCAGATTTGAGCCTGGGAGCTCTCT
                  .         .         .         9100      .         B ←
        GCTAGCTAGGGAACCCACTGCTTAAGCCTCAATAAAGCTTGCCTTGAGTGCTTCAA |
                  .         .         .         .         .
```

VARIANT OF LAV VIRUSES

This is a continuation of application Ser. No. 08/423,477, filed Apr. 19, 1995, which is a division of application Ser. No. 07/656,796, filed Feb. 19, 1991 now U.S. Pat. No. 5,869,631, which is a division of application Ser. No. 07/038,332, filed Apr. 13, 1987, now U.S. Pat. No. 5,034,511, all of which are incorporated herein by reference.

BACKGROUND OF THE INVENTION

The present invention relates to a virus capable of inducing lymphadenopathies (hereinafter "LAS") and acquired immuno-depressive syndromes (hereinafter "AIDS"), to antigens of this virus, particularly in a purified form, and to a process for producing these antigens, particularly antigens of the envelope of this virus. The invention also relates to polypeptides, whether glycosylated or not, produced by the virus and to DNA sequences which code for such polypeptides. The invention further relates to cloned DNA sequences hybridizable to genomic RNA and DNA of the lymphadenopathy associated virus (hereinafter "LAV") of this invention and to processes for their preparation and their use. The invention still further relates to a stable probe including a DNA sequence which can be used for the detection of the LAV virus of this invention or related viruses or DNA proviruses in any medium, particularly biological, and in samples containing any of them.

An important genetic polymorphism has been recognized for the human retrovirus which is the cause of AIDS and other diseases like LAS, AIDS-related complex (hereinafter "ARC") and probably some encephalopathies (for review, see Weiss, 1984). Indeed all of the isolates, analyzed until now, have had distinct restriction maps, even those recovered at the same place and time [Benn et al., 1985]. Identical restriction maps have only been observed for the first two isolates which were designated LAV [Alizon et al., 1984] and human T-cell lymphotropic virus type 3 (hereinafter "HTLV-3") [Hahn et al., 1984] and which appear to be exceptions. The genetic polymorphism of the AIDS virus was better assessed after the determination of the complete nucleotide sequence of LAV [Wain-Hobson et al., 1985], HTLV-3 [Ratner et al., 1985; Muesing et al., 1985] and a third isolate designated AIDS-associated retrovirus (hereinafter "ARV 2") [Sanchez-Pescador et al., 1985]. In particular, it appeared that, besides the nucleic acid variations responsible for the restriction map polymorphism, isolates could differ significantly at the protein level, especially in the envelope (up to 13% of difference between ARV and LAV), by both amino acids substitutions and reciprocal insertions-deletions [Rabson and Martin, 1985].

Nevertheless, such differences did not go so far as to destroy the immunological similarity of such isolates as evidenced by the capabilities of their similar proteins, (e.g., core proteins of similar nature, such as the p25 proteins, or similar envelope glycoproteins, such as the 110–120 kD glycoproteins) to immunologically cross-react. Accordingly, the proteins of any of said LAV viruses can be used for the in vitro detection of antibodies induced in vivo and present in biological fluids obtained from individuals infected with the other LAV variants. Therefore, these viruses are grouped together as a class of LAV viruses (hereinafter "LAV-1 viruses").

SUMMARY OF THE INVENTION

In accordance with this invention, a new virus has been discovered that is responsible for diseases clinically related to AIDS and that can be classified as a LAV-1 virus but that differs genetically from known LAV-1 viruses to a much larger extent than the known LAV-1 viruses differ from each other. The new virus is basically characterized by the cDNA sequence which is shown in FIGS. 7A to 7I, and this new virus is hereinafter generally referred to as "$LAV_{ELI}$".

Also in accordance with this invention, variants of the new virus are provided. The RNAs of these variants and the related cDNAs derived from said RNAs are hybridizable to corresponding parts of the cDNA of $LAV_{ELI}$. The DNA of the new virus also is provided, as well as DNA fragments derived therefrom hybridizable with the genomic RNA of $LAV_{ELI}$ such DNA and DNA fragments particularly consisting of the cDNA or cDNA fragments of $LAV_{ELI}$ or of recombinant DNAs containing such cDNA or cDNA fragments.

DNA recombinants containing the DNA or DNA fragments of $LAV_{ELI}$ or its variants are also provided. It is of course understood that fragments which would include some deletions or mutations which would not substantially alter their capability of also hybridizing with the retroviral genome of $LAV_{ELI}$ are to be considered as forming obvious equivalents of the DNA or DNA fragments referred to hereinabove.

Cloned probes are further provided which can be made starting from any DNA fragment according to the invention, as are recombinant DNAs containing such fragments, particularly any plasmids amplifiable in procaryotic or eucaryotic cells and carrying said fragments. Using cloned DNA containing a DNA fragment of $LAV_{ELI}$ as a molecular hybridization probe—either by marking with radionucleotides or with fluorescent reagents—LAV virion RNA may be detected directly, for example, in blood, body fluids and blood products (e.g., in antihemophylic factors such as Factor VIII concentrates). A suitable method for achieving such detection comprises immobilizing $LAV_{ELI}$ on a support (e.g., a nitrocellulose filter), disrupting the virion and hybridizing with a labelled (radiolabelled or "cold" fluorescent- or enzyme-labelled probe. Such an approach has already been developed for Hepatitis B virus in peripheral blood (according to Scotto J. et al. Hepatology (1983), 3, 379–384).

Probes according to the invention can also be used for rapid screening of genomic DNA derived from the tissue of patients with LAV related symptoms to see if the proviral DNA or RNA present in their tissues is related to $LAV_{ELI}$. A method which can be used for such screening comprises the following steps: extraction of DNA from tissue, restriction enzyme cleavage of said DNA, electrophoresis of the fragments and Southern blotting of genomic DNA from tissues and subsequent hybridization with labelled cloned LAV proviral DNA. Hybridization in situ can also be used. Lymphatic fluids and tissues and other non-lymphatic tissues of humans, primates and other mammalian species can also be screened to see if other evolutionary related retroviruses exist. The methods referred to hereinabove can be used, although hybridization and washings would be done under non-stringent conditions.

The DNA according to the invention can be used also for achieving the expression of LAV viral antigens for diagnostic purposes, as well as for the production of a vaccine against LAV. Fragments of particular advantage in that respect will be discussed later. The methods which can be used are multifold:

a) DNA can be transfected into mammalian cells with appropriate selection markers by a variety of techniques, such as calcium phosphate precipitation, polyethylene glycol, protoplast-fusion, etc.

b) DNA fragments corresponding to genes can be cloned into expression vectors for *E. coli*, yeast or mammalian cells and the resultant proteins purified.

c) The proviral DNA can be "shot-gunned" (fragmented) into procaryotic expression vectors to generate fusion polypeptides.

Recombinants, producing antigenically competent fusion proteins, can be identified by simply screening the recombinants with antibodies against $LAV_{ELI}$ antigens. Particular reference in this respect is made to those portions of the genome of $LAV_{ELI}$ which, in the figures, are shown to belong to open reading frames and which encode the products having the polypeptidic backbones shown.

Different polypeptides which appear in FIGS. 7A to 7I are still further provided. Methods disclosed in European application O 178 978 and in PCT application PCT/EP 85/00548, filed Oct. 18, 1985, are applicable for the production of such peptides from $LAV_{ELI}$. In this regard, polypeptides are provided containing sequences in common with polypeptides comprising antigenic determinants included in the proteins encoded and expressed by the $LAV_{ELI}$ genome. Means are also provided for the detection of proteins of $LAV_{ELI}$ particularly for the diagnosis of AIDS or pre-AIDS or, to the contrary, for the detection of antibodies against $LAV_{ELI}$ or its proteins, particularly in patients afflicted with AIDS or pre-AIDS or more generally in asymtomatic carriers and in blood-related products. Further provided are immunogenic polypeptides and more particularly protective polypeptides for use in the preparation of vaccine compositions against AIDS or related syndroms.

Yet further provided are polypeptide fragments having lower molecular weights and having peptide sequences or fragments in common with those shown in FIGS. 7A to 7I. Fragments of smaller sizes can be obtained by resorting to known techniques, for instance, by cleaving the original larger polypeptide by enzymes capable of cleaving it at specific sites. By way of examples may be mentioned the enzyme of *Staphylococcyus aureus* V8, α-chymotrypsin, "mouse sub-maxillary gland protease" marketed by the Boehringer company, *Vibrio alginolyticus chemovar iophagus* collagenase, which specifically recognizes the peptides Gly-Pro, Gly-Ala, etc.

Other features of this invention will appear in the following disclosure of data obtained starting from $LAV_{ELI}$, in relation to the drawings.

BRIEF DESCRIPTION OF THE DRAWINGS

FIGS. 1A and 1B provide comparative restriction maps of the genomas of $LAV_{ELI}$ as compared to $LAV_{MAL}$ (Applicants' related new LAV virus which is the subject of their copending application, filed herewith) and $LAV_{BRU}$ (a known LAV isolate deposited at the Collection Nationale des Cultures de Micro-organismes (hereinafter "CNCM") of the Pasteur Institute, Paris, France under No. I-232 on Jul. 15, 1983);

Figure 3A:
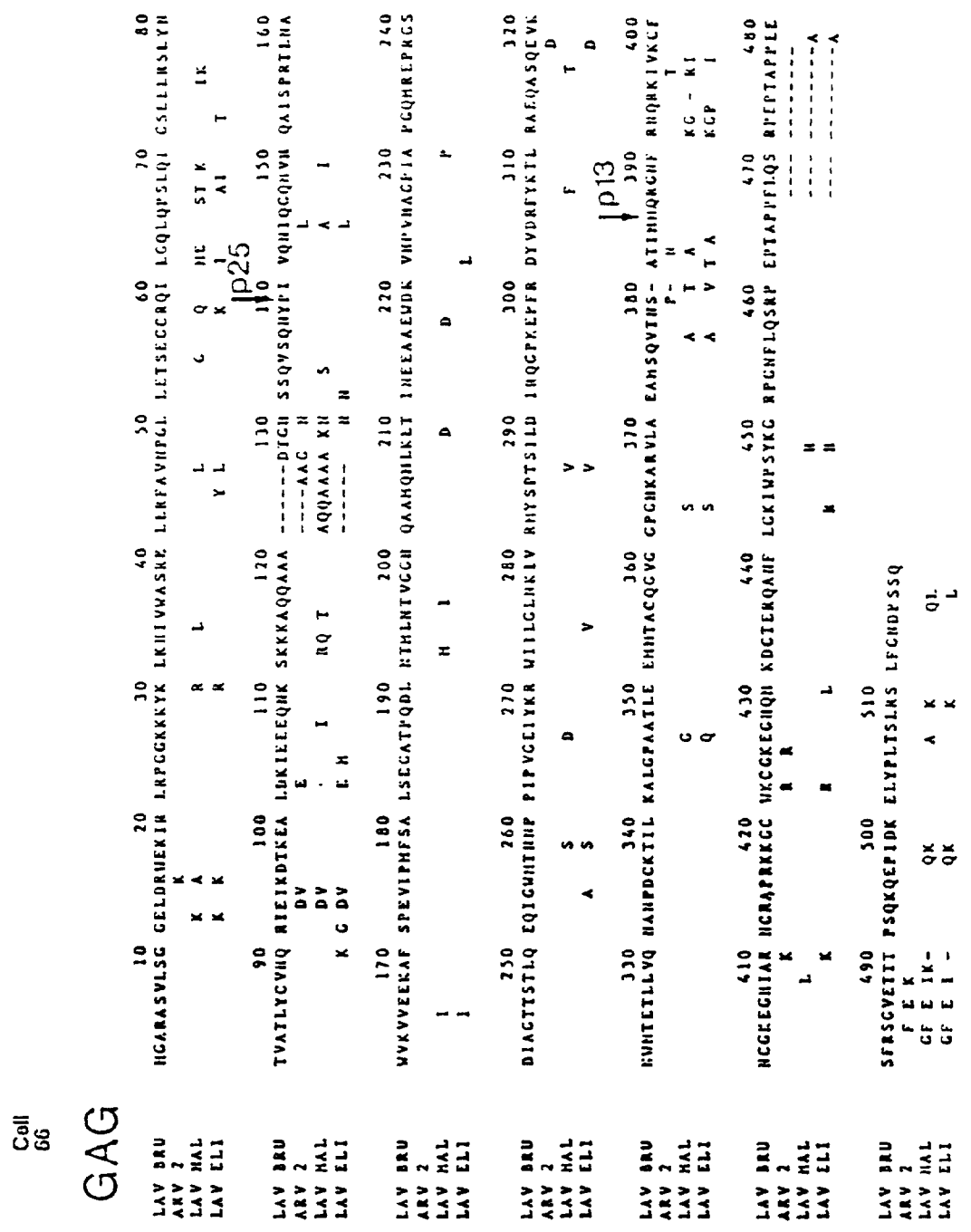
Figure 3B:
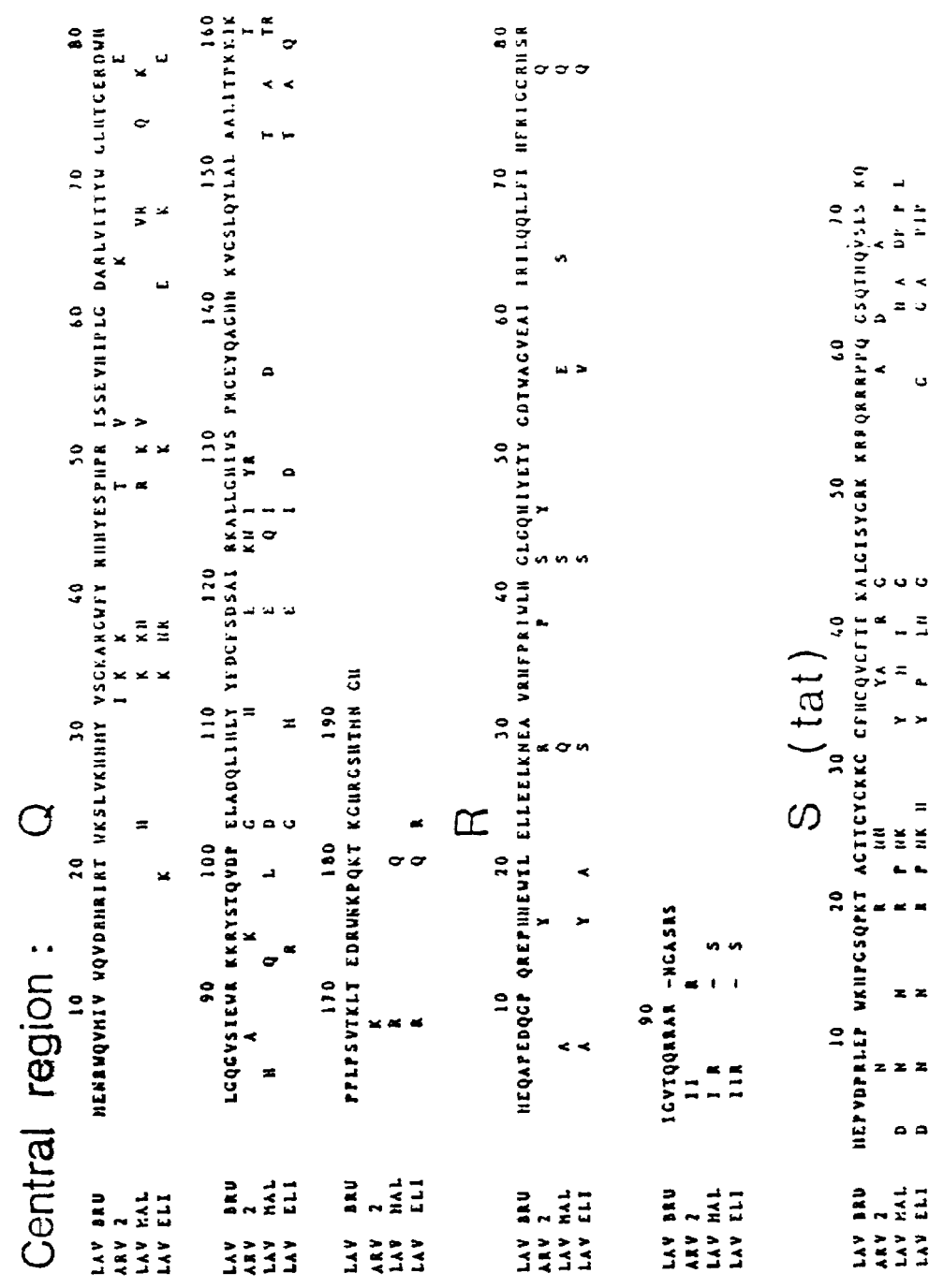
Figure 3C:
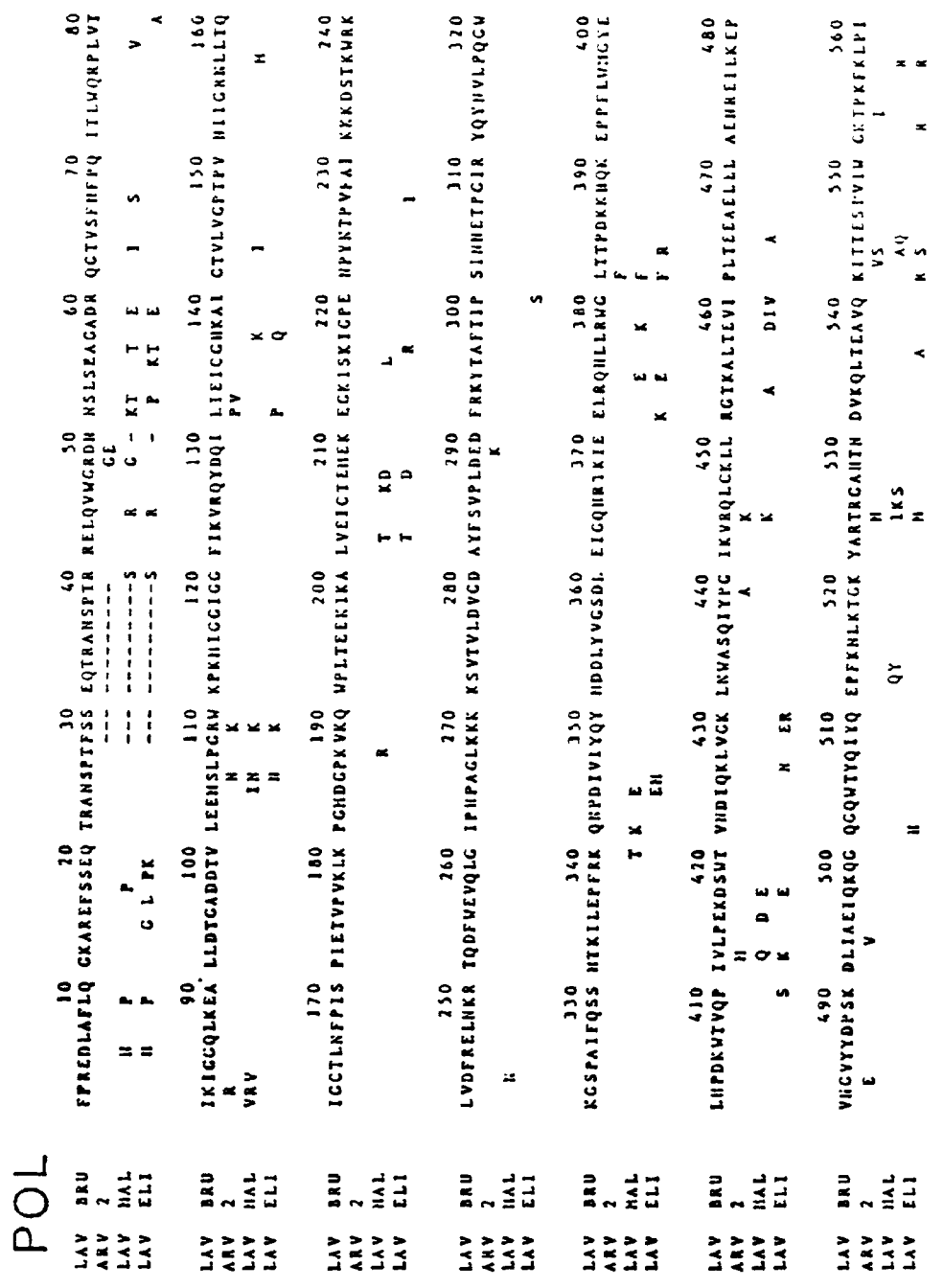
Figure 3D:
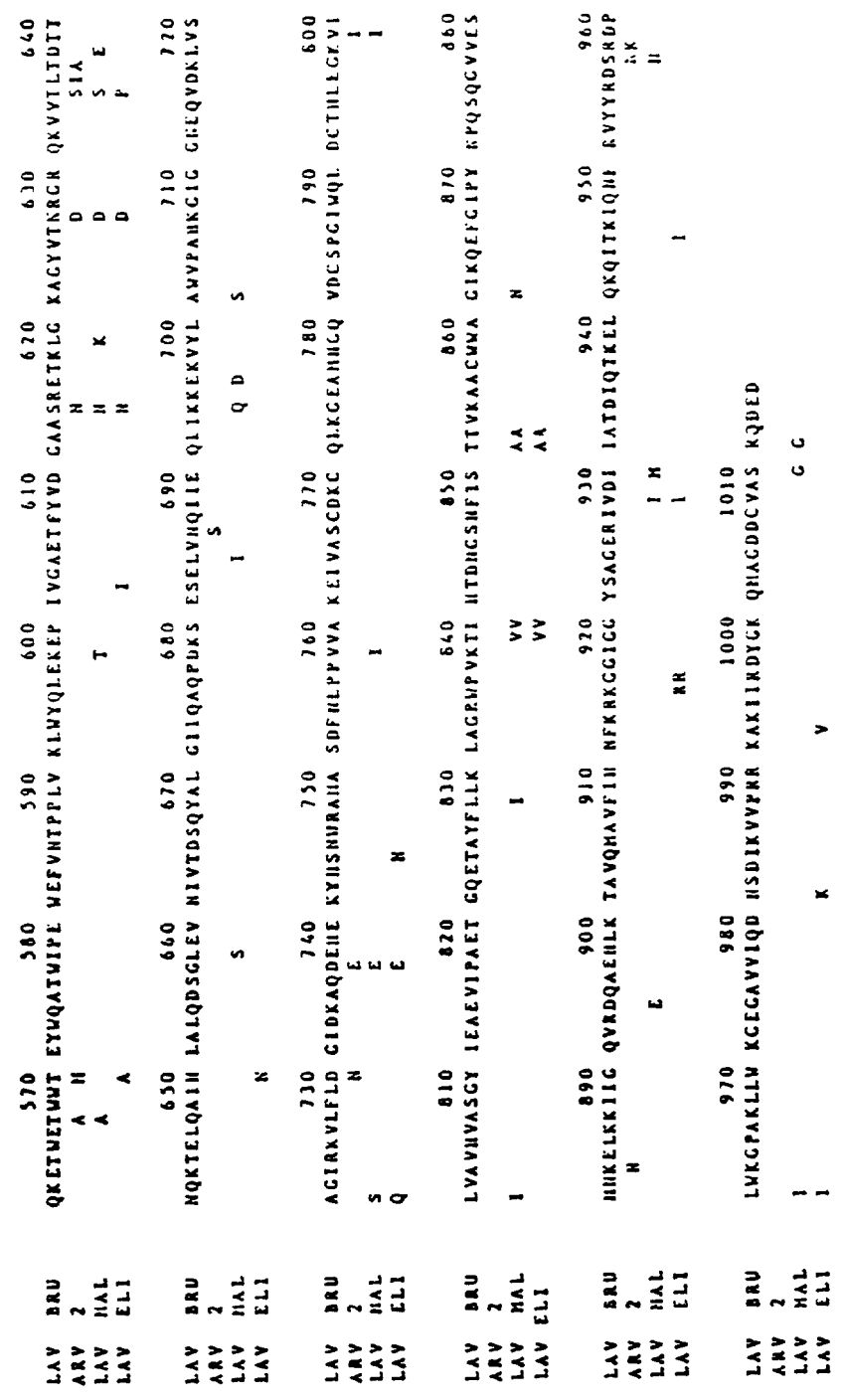
Figure 3E:
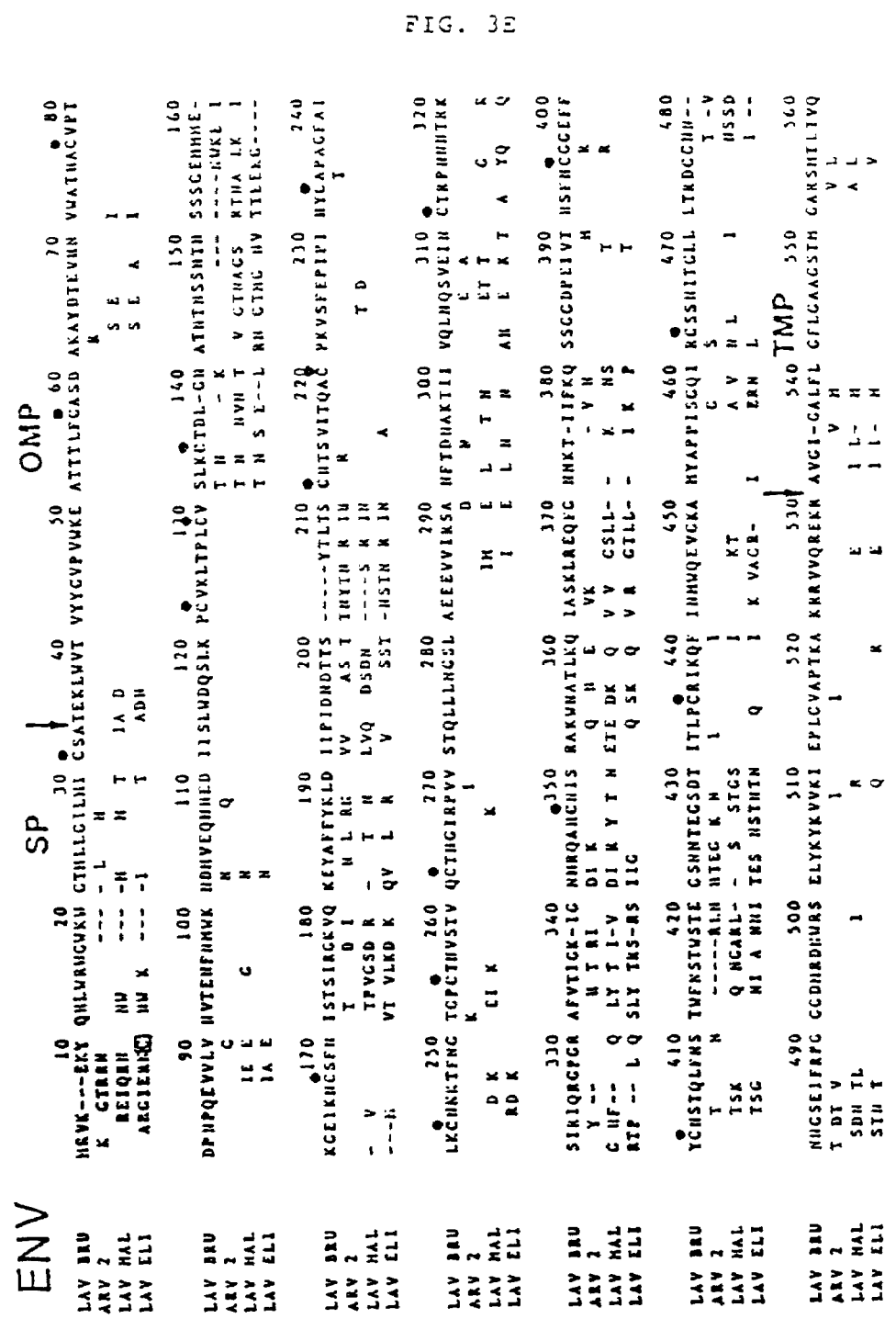
Figure 3F:
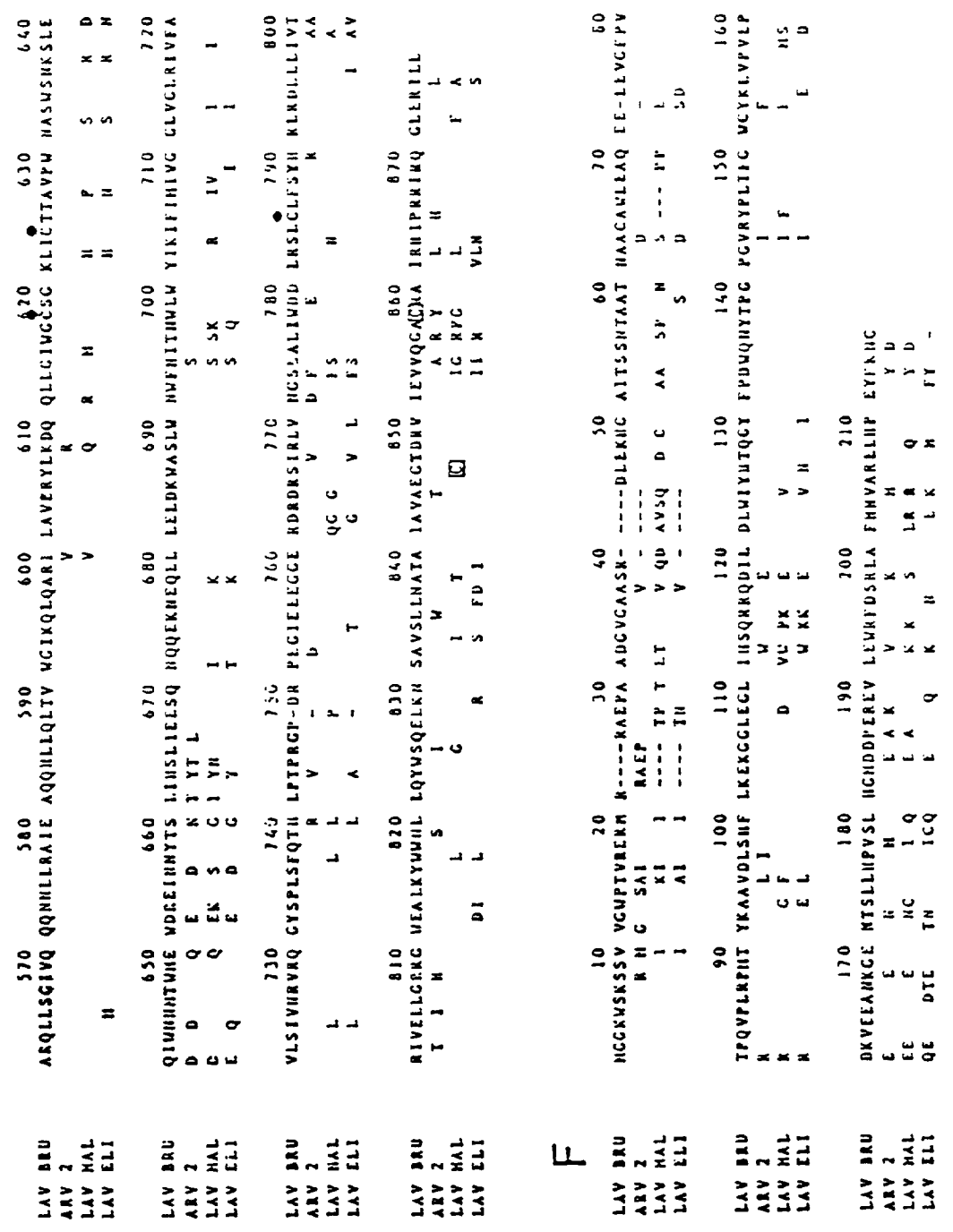

FIGS. 3A–3F (also designated generally hereinafter "FIG. 3") indicate the relative correspondence between the proteins (or glycoproteins) encoded by the open reading frames, whereby amino acid residues of protein sequences of $LAV_{ELI}$ are in vertical alignment with corresponding amino acid residues (numbered) of corresponding or homologous proteins or glycoproteins of $LAV_{BRU}$, as well as $LAV_{MAL}$ and ARV 2;

FIGS. 4A–4B (also designated generally hereinafter "FIG. 4") provide tables quantitating the sequence divergence between homologous proteins of $LAV_{BRU}$, $LAV_{ELI}$ and $LAV_{MAL}$;

FIGS. 6A and 6B ("FIG. 6" when consulted together) render apparent the direct repeats which appear in the proteins of the different AIDS virus isolates.

FIGS. 7A–7I show the full nucleotidic sequences of $LAV_{ELI}$.

DETAILED DESCRIPTION OF THE INVENTION

Figure 2:
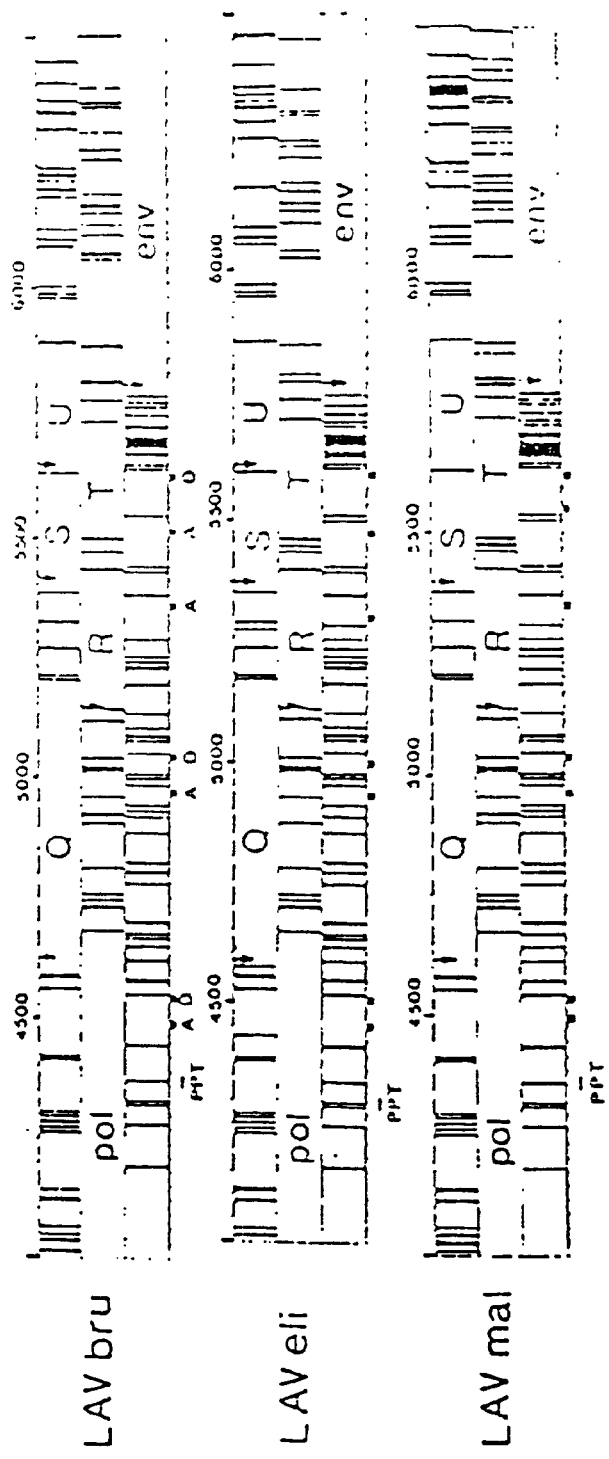
FIG. 2 shows comparative maps setting forth the relative positions of the open reading frames of the above genomas.

Characterization and Molecular Cloning of an African Isolate.

The different AIDS virus isolates concerned are designated by three letters of the patients name, $LAV_{BRU}$ referring to the prototype AIDS virus isolated in 1983 from a French homosexual patient with LAS and thought to have been infected in the USA in the preceding years [Barré-Sinoussi et al., 1983]. $LAV_{ELI}$ was recovered in 1983 from a 24-year old woman with AIDS from Zaire. Related $LAV_{MAL}$ was recovered in 1985 from a 7-year old boy from Zaire. Recovery and purification of the $LAV_{ELI}$ virus were performed according to the method disclosed in European Patent Application 84 401834/138667 filed on Sep. 9, 1984.

$LAV_{ELI}$ is indistinguishable from the previously characterized isolates by its structural and biological properties in vitro. Virus metabolic labelling and immune precipitation by patient ELI sera, as well as reference sera, showed that the proteins of $LAV_{ELI}$ had the same molecular weight (hereinafter "MW") as, and cross-reacted immunologically with those of, prototype AIDS virus (data not shown) of the LAV-1 class.

Reference is again made to European Application 178 978 and International Application PCT/EP 85/00548 as concerns the purification, mapping and sequencing procedures used herein. See also the discussion under the headings "Experimental Procedures" and "Significance of the Figures" hereinafter.

Primary restriction enzyme analysis of $LAV_{ELI}$ genome was done by southern blot with total DNA derived from acutely infected lymphocytes, using cloned $LAV_{BRU}$ complete genome as probe. Overall cross-hybridization was observed under stringent conditions, but the restriction profile of the Zairian isolate was clearly different. Phage lambda clones carrying the complete viral genetic information were obtained and further characterized by restriction mapping and nucleotide sequence analysis. A Clone (hereinafter "E-H12") was derived from $LAV_{ELI}$ infected cells and contained an integrated provirus with 5' flanking cellular sequences but a truncated 3' long terminal repeat (hereinafter "LTR").

FIG. 1B gives a comparaison of the restriction maps derived from the nucleotide sequences of $LAV_{ELI}$, $LAV_{MAL}$ and prototype $LAV_{BRU}$, as well as from three other Zairian isolates (hereinafter "Z1", "Z2", and "Z3" respectively)

previously mapped for seven restriction enzymes [Benn et al., 1985]. Despite this limited number, all of the profiles are clearly different (out of the 23 sites making up the map of $LAV_{BRU}$, only seven are present in all six maps presented), confirming the genetic polymorphism of the AIDS virus. No obvious relationship is apparent between the five Zairian maps, and all of their common sites are also found in $LAV_{BRU}$.

Conservation of the Genetic Organization.

The genetic organization of $LAV_{ELI}$ as deduced from the complete nucleotide sequences of its cloned genome is identical to that found in other isolates, i.e., 5'gag-pol-central region-env-F3'. Most noticeable is the conservation of the "central region" (FIG. 2), located between the pol and env genes, which is composed of a series of overlapping open reading frames (hereinafter "orf") previously designated Q, R, S, T, and U in the ovine lentivirus visna [Sonigo et al., 1985]. The product of orf S (also designated "tat") is implicated in the transactivation of virus expression [Sodroski et al., 1985; Arya et al., 1985]; the biological role of the product of orf Q (also designated "sor" or "orf A") is still unknown [Lee et al., 1986; Kang et al., 1986]. Of the three other orfs, R, T, and U, only orf R is likely to be a seventh viral gene, for the following reasons: the exact conservation of its relative position with respect to Q and S (FIG. 2), the ponstant presence of a possible splice acceptor and of a consensus AUG initiator codon, its similar codon usage with respect to viral genes, and finally the fact that the variation of its protein sequence within the different isolates is comparable to that of gag, pol and Q (see FIG. 4).

Also conserved are the sizes of the U3, R and U5 elements of the LTR (data not shown), the location and sequence of their regulatory elements such as TATA box and AATAAA polyadenylation signal, and their flanking sequences, i.e., primer binding site (hereinafter "PBS") complementary to 3' end of $tRNA^{LYS}$ and polypurine tract (hereinafter "PPT"). Most of the genetic variability within the LTR is located in the 5' half of U3 (which encodes a part of orf F) while the 3' end of U3 and R, which carry most of the cis-acting regulatory elements, promoter, enhancer and trans-activating factor receptor [Rosen et al., 1985], as well as the U5 element, are well-conserved.

Overall, it clearly appears that this Zairian isolate, $LAV_{ELI}$, is the same type of retrovirus as the previously sequenced isolates of American or European origin.

Variability of the Viral Proteins.

Despite their identical genetic organization, the $LAV_{ELI}$ and $LAV_{MAL}$ shows substantial differences in the primary structure of their proteins. The amino acid sequences of $LAV_{ELI}$ and $LAV_{MAL}$ proteins are presented in FIGS. 3A–3F, aligned with those of $LAV_{BRU}$ and ARV 2. Their divergence was quantified as the percentage of amino acids substitutions in two-by-two alignments (FIG. 4). The number of insertions and deletions that had to be introduced in each of these alignments has also been scored.

Three general observations can be made. First, the protein sequences of the $LAV_{ELI}$ and $LAV_{MAL}$ are more divergent from $LAV_{BRU}$ than are those of HTLV-3 and ARV 2 (FIG. 4A); similar results are obtained if ARV 2 is taken as reference (not shown). The range of genetic polymorphism between isolates of the AIDS virus is considerably greater than previously observed. Second, our two sequences confirm that the envelope is more variable than the gag and pol genes. Here again, the relatively small difference observed between the env of $LAV_{BRU}$ and HTLV-3 appears as an exception. Third, the mutual divergence of the $LAV_{ELI}$ and $LAV_{MAL}$ (FIG. 4B) is comparable to that between $LAV_{BRU}$ and either of them; as far as we can extrapolate from only three sequenced isolates from the USA and Europe and two ($LAV_{ELI}$ and $LAV_{MAL}$) from Africa, this is indicative of a wider evolution of the AIDS virus in Africa.

gag and pol: Their greater degree of conservation compared to the envelope is consistent with their encoding important structural or enzymatic activities. Of the three mature gag proteins, the p25 which was the first recognized immunogenic protein of LAV [Barré-Sinoussi et al., 1983] is also the better conserved (FIG. 3). In gag and pol, differences between isolates are principally due to point mutations, and only a small number of insertional or deletional events is observed. Among these, we must note the presence in the overlapping part of gag and pol of $LAV_{BRU}$ of an insertion of 12 amino acids (AA) which is encoded by the second copy of a 36 bp direct repeat present only in this isolate and in HTLV-3. This duplication was omitted because of a computing error in the published sequence of $LAV_{BRU}$ (position 1712, Wain-Hobson et al., 1985) but was indeed present in the HTLV-3 sequences [Ratner et al., 1985; Muesing et al., 1985].

env: Three segments can be distinguished in the envelope glycoprotein precursor [Allan et al., 1985; Montagnier et al., 1985; DiMarzoVeronese et al., 1985]. The first is the signal peptide (positions 1–33 in FIG. 3), and its sequence appears as variable; the second segment (pos. 34–530) forms the outer membrane protein (hereinafter "OMP" or "gp110") and carries most of the genetic variations, and in particular almost all of the numerous reciprocal insertions and deletions; the third segment (531–877) is separated from the OMP by a potential cleavage site following a constant basic stretch (Arg-Glu-Lys-Arg) and forms the transmembrane protein (hereinafter "TMP" or "gp 41") responsible for the anchorage of the envelope glycoprotein in the cellular membrane. A better conservation of the TMP than the OMP has also been observed between the different murine leukemia viruses (hereinafter "MLV") [Koch et al., 1983] and could be due to structural constraints.

Figure 5:
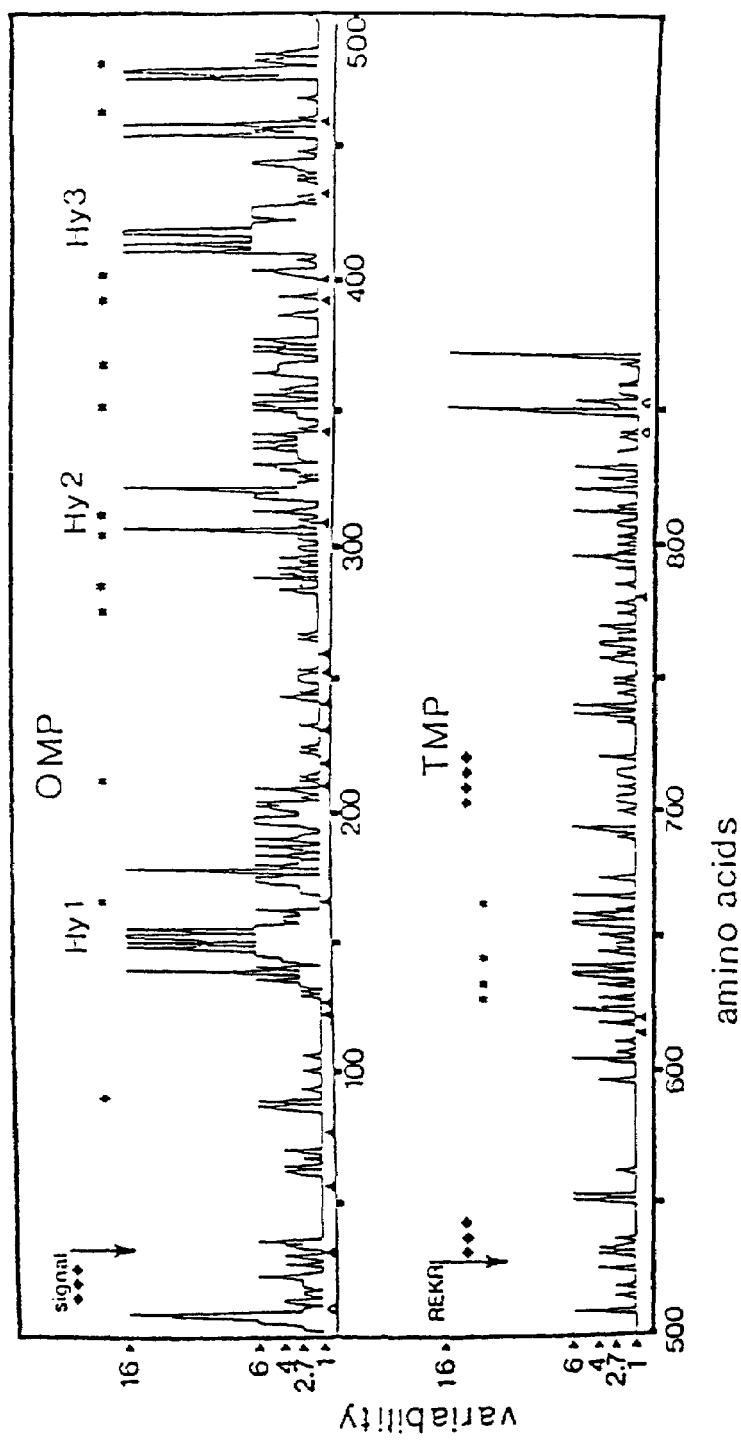
FIG. 5 shows diagrammatically the degree of divergence of the different virus envelope proteins.

From the alignment of FIG. 3 and the graphical representation of the envelope variability shown in FIG. 5, we clearly see the existence of conserved domains, with little or no genetic variation, and hypervariable domains, in which even the alignment of the different sequences is very difficult, because of the existence of a large number of mutations and of reciprocal insertions and deletions. We have not included the sequence of the envelope of the HTLV-3 isolate since it so close to that of $LAV_{BRU}$ (cf. FIG. 4), even in the hypervariable domains, that it did not add anything to the analysis. While this graphical representation will be refined by more sequence data, the general profile is already apparent, with three hypervariable domains (Hyl, 2 and 3) all being located in the OMP and separated by three well-conserved stretches (residues 37–130, 211–289, and 488–530 of FIG. 3 alignment) probably associated with important biological functions.

In spite of the extreme genetic variability, the folding pattern of the envelope glycoprotein is probably constant. Indeed the position of virtually all of the cysteine residues is conserved within the different isolates (FIGS. 3 and 5), and the only three variable cysteines fall either in the signal peptide or in the very C-terminal part of the TMP. The hypervariable domains of the OMP are bounded by conserved cysteines, suggesting that they may represent loops attached to the common folding pattern. Also the calculated hydropathic profiles [Kyte and Doolittle, 1982] of the different envelope proteins are remarkably conserved (not shown).

About half of the potential N-glycosylation sites, Asn-X-Ser/Thr, found in the envelopes of the Zairian isolates map to the same positions in $LAV_{BRU}$ (17/26 for $LAV_{ELI}$ and 17/28 for $LAV_{MAL}$). The other sites appear to fall within variable domains of env, suggesting the existence of differences in the extent of envelope glycosylation between different isolates.

Other viral proteins: Of the three other identified viral proteins, the p27 encoded by orf F, 3' of env [Allan et al., 1985b] is the most variable (FIG. 4). The proteins encoded by orfs Q and S of the central region are remarkable by their absence of insertions/deletions. Surprisingly, a high frequency of amino acids substitutions, comparable to that observed in env, is found for the product of orf S (trans-activating factor). On the other hand, the protein encoded by orf Q is no more variable than gag. Also noticeable is the lower variation of the proteins encoded by the central regions of $LAV_{ELI}$ and $LAV_{MAL}$.

With the availability of the complete nucleotide sequence from five independent isolates, some general features of the AIDS virus' genetic variability are now emerging. Firstly, its principal cause is point mutations which very often result in amino acid substitutions and which are more frequent in the 3' part of the genome (orf S, env and orf F). Like all RNA viruses, the retroviruses are thought to be highly subject to mutations caused by errors of the RNA polymerases during their replication, since there is no proofreading, of this step [Holland et al., 1982; Steinhauer and Holland, 1986].

Figure 6A:
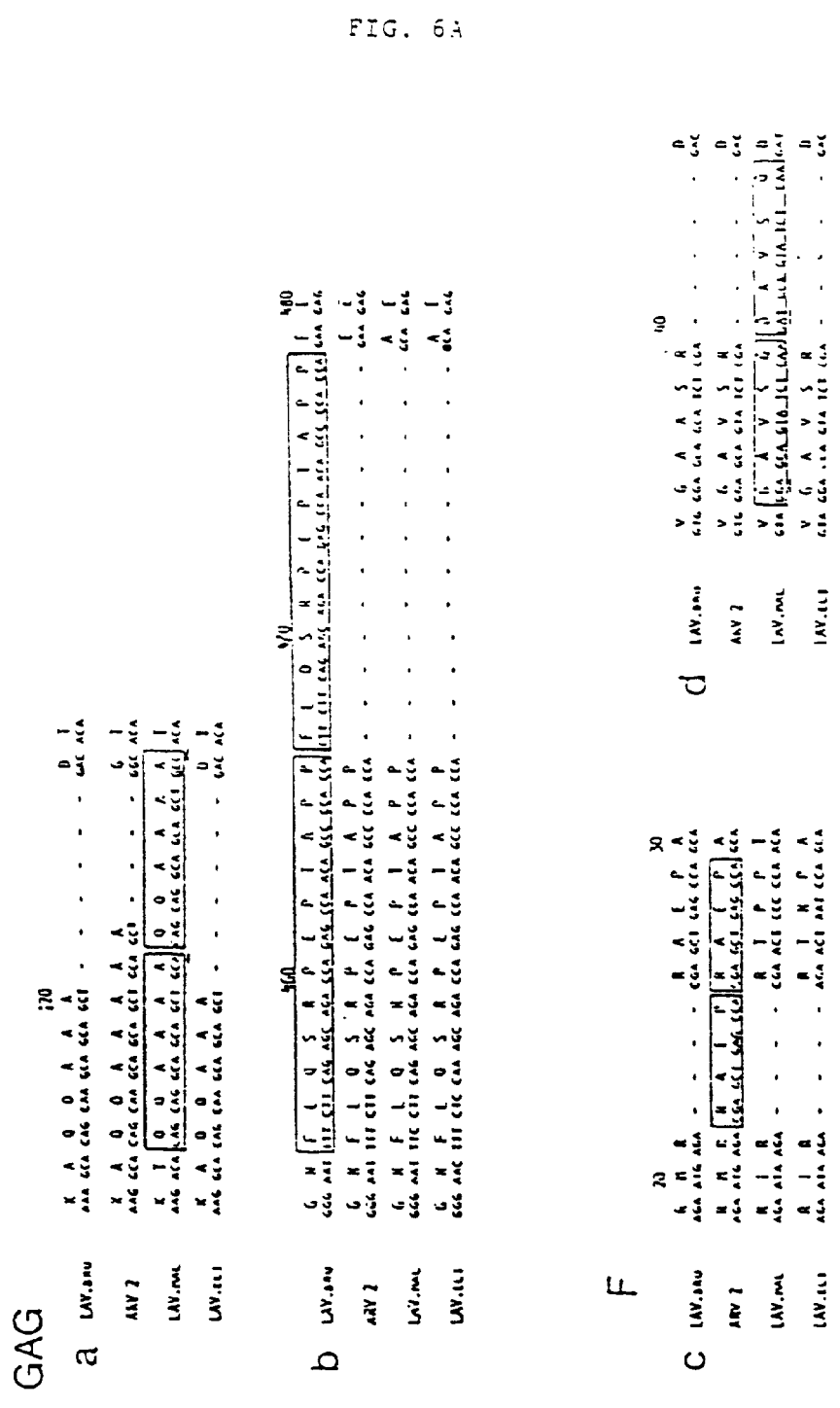
Figure 6B:
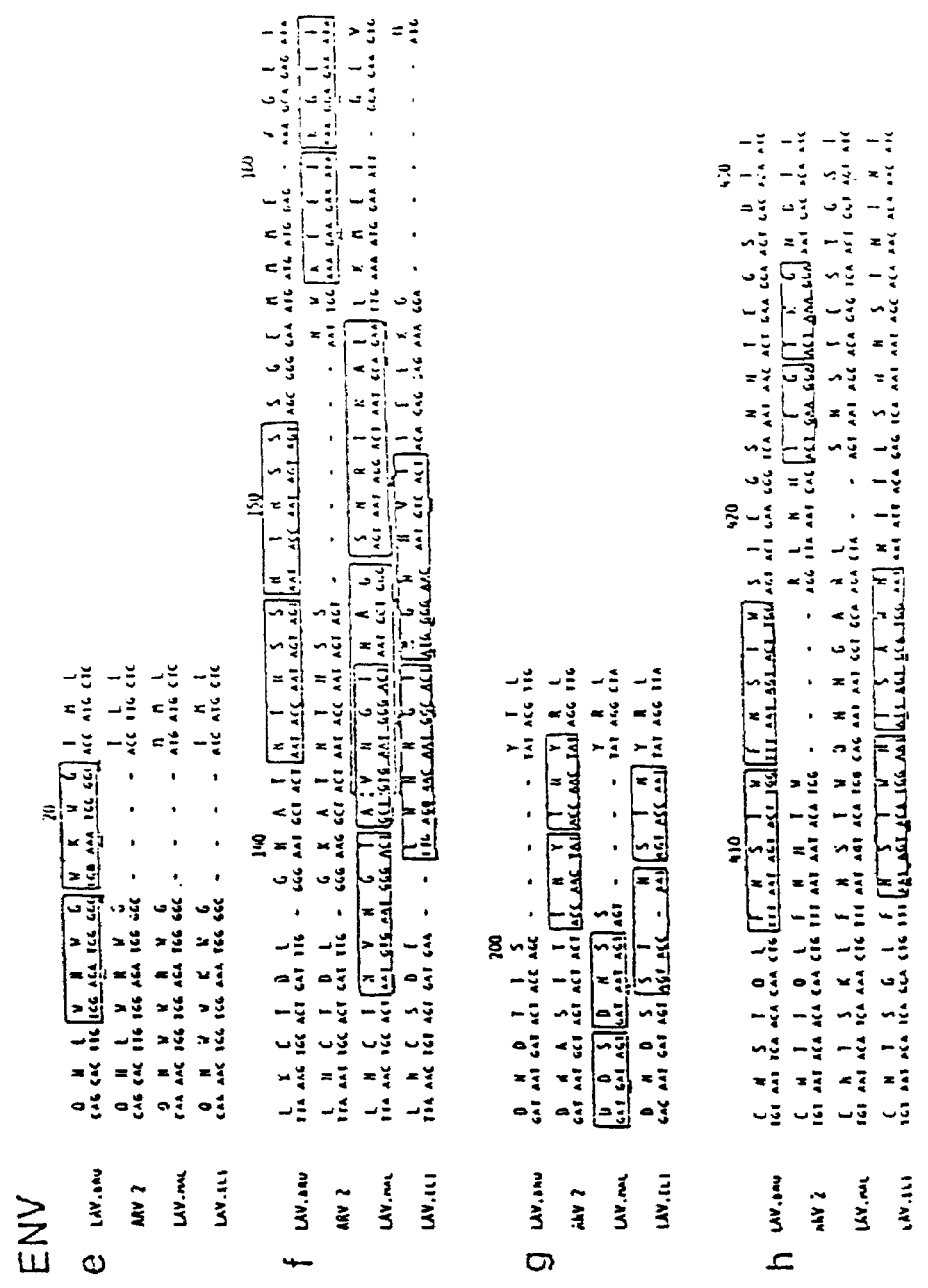

Another source of genetic diversity is insertions/deletions. From the FIG. 3 alignments, insertional events seem to be implicated in most of the cases, since otherwise deletions should have occurred in independent isolates at precisely the same locations. Furthermore, upon analyzing these insertions, we have observed that they most often represent one of the two copies of a direct repeat (FIG. 6). Some are perfectly conserved like the 36 bp repeat in the gag-pol overlap of $LAV_{BRU}$ (FIG. 6-a); others carry point mutations resulting in amino acid substitutions, and as a consequence, they are more difficult to observe, though clearly present, in the hypervariable domains of env (cf. FIGS. 6-g and -h). As noted for point mutations, env gene and orf F also appear as more susceptible to that form of genetic variation than the rest of the genome. The degree of conservation of these repeats must be related to their date of occurrence in the analyzed sequences: the more degenerated, the more ancient. A very recent divergence of $LAV_{BRU}$ and HTLV-3 is suggested by the extremely low number of mismatched AA between their homologous proteins. However, one of the $LAV_{BRU}$ repeats (located in the Hy1domain of env, FIG. 6-f) is not present in HTLV-3, indicating that this generation of tandem repeats is a rapid source of genetic diversity. We have found no traces of such a phenomenon, even when comparing very closely related viruses, such as the Mason-Pfizer monkey virus (hereinafter "MPMV") [Sonigo et al., 1986], and an immunosuppressive simian virus (hereinafter "SRV-1") [Power et al., 1986]. Insertion or deletion of one copy of a direct repeat have been occasionally reported in mutant retroviruses [Shimotohno and Temin, 1981; Darlix, 1986], but the extent to which we observe this phenomenon is unprecedented. The molecular basis of these duplications is unclear, but could be the "copy-choice" phenomenon, resulting from the diploidy of the retroviral genome [Varmus and Swanstrom, 1984; Clark and Mak, 1983]. During the synthesis of the first-strand of the viral DNA, jumps are known to occur from one RNA molecule to another, especially when a break or a stable secondary structure is present on the template; an inaccurate re-initiation on the other RNA template could result in the generation (or the elimination) of a short direct repeat.

Genetic variability and subsequent antigenic modifications have often been developed by micro-organisms as a means for avoiding the host's immune response, either by modifying their epitopes during the course of the infection, as in trypanosomes [Borst and Cross, 1982], or by generating a large repertoire of antigens, as observed in influenza virus [Webster et al., 1982]. As the human AIDS virus is related to animal lentiviruses [Sonigo et al., 1985; Chiu et al., 1985], its genetic variability could be a source of antigenic variation, as can be observed during the course of the infection by the ovine lentivirus visna [Scott et al., 1979; Clements et al., 1980] or by the equine infectious anemia virus (hereinafter "EIAV") [Montelaro et al., 1984]. However, a major discrepancy with these animal models is the extremely low, and possibly nonexistent, neutralizing activity of the sera of individuals infected by the AIDS virus, whether they are healthy carriers, displaying minor symptoms, or afflicted with AIDS [Weiss et al., 1985; Clavel et al., 1985]. Furthermore, even for the visna virus the exact role of antigenic variation in the pathogenesis is unclear [Thormar et al., 1983; Lutley et al., 1983]. We rather believe that genetic variation represents a general selective advantage for lentiviruses by allowing an adaptation to different environments, for example by modifying their tissue or host tropisms. In the particular case of the AIDS virus, rapid genetic variations are tolerated, especially in the envelope. This could allow the virus to become adapted to different "micro-environments" of the membrane of their principal target cells, namely the T4 lymphocytes. These "micro-environments" could result from the immediate vicinity of the virus receptor to polymorphic surface proteins, differing either between individuals or between clones of lymphocytes.

Conserved Domains in the AIDS Virus Envelope

Since the proteins of most of the isolates are antigenically cross-reactive, the genotypic differences do not seem to affect the sensitivity of actual diagnostic tests, based upon the detection of antibodies to the AIDS virus and using purified virions as antigens. They nevertheless have to be considered for the development of the "second-generation" tests, that are expected to be more specific, and will use smaller synthetic or genetically-engineered viral antigens. The identification of conserved domains in the highly immunogenic envelope glycoprotein and the core structural proteins (gag) is very important for these tests. The conserved stretch found at the end of the OMP and the beginning of the TMP (490–620, FIG. 3) could be a good candidate, since a bacterial fusion protein containing this domain was well-detected by AIDS patients' sera [Chang et al., 1985].

The envelope, specifically the OMP, mediates the interaction between a retrovirus and its specific cellular receptor [DeLarco and Todaro, 1976; Robinson et al., 1980]. In the case of the AIDS virus, in vitro binding assays have shown the interaction of the envelope glycoprotein gp110 with the T4 cellular surface antigen [McDougal et al., 1986], already thought to be closely associated with the virus receptor [Klatzmann et al., 1984; Dagleish et al., 1984]. Identification of the AIDS virus envelope domains that are responsible for this interaction (receptor-binding domains) appears to be fundamental for understanding of the host-viral interactions and for designing a protective vaccine, since an immune response against these epitopes could possibly elicit neutralizing antibodies. As the AIDS virus receptor is at least partly formed of a constant structure, the T4 antigen, the binding site of the envelope is unlikely to be exclusively encoded by domains undergoing drastic genetic changes between isolates, even if these could be implicated in some kind of an "adaptation". One or several of the conserved domains of the OMP (residues 37–130, 211–289, and 488–530 of FIG. 3 alignment), b:ought together by the folding of the protein, must play a part in the virus-receptor interaction, and this can be explored with synthetic or genetically-engineered peptides derived from these domains, either by direct binding assays or indirectly by assaying the neutralizing activity of specific antibodies raised against them.

African AIDS Viruses

Zaire and the neighboring countries of Central Africa are considered as an area endemic with the AIDS virus infection, and the possibility that the virus has emerged in Africa has became a subject of intense controversy (see Norman, 1985). From the present study, it is clear that the genetic organization of Zairian isolates is the same as that of american isolates, thereby indicating a common origin. The very important sequence differences observed between the proteins are consistent with a divergent evolutionary process. In addition, the two African isolates are mutually more divergent than the American isolates already analyzed as far as that observation can be extrapolated, it suggests a longer evolution of the virus in Africa and is also consistent with the fact that a larger fraction of the population is exposed than in developed countries.

A novel human retrovirus with morphology and biologocal properties (cytopathogenicity, T4 tropism) similar to those of LAV, but nevertheless clearly genetically and antigenically distinct from it, was recently isolated from two patients with AIDS originating from Guinea Bissau, West-Africa [Clavel et al., 1986]. In neighboring Senegal, the population was seemingly exposed to a retrovirus also distinct from LAV but apparently non-pathogenic [Barin et al., 1985; Kanki et al., 1986]. Both of these novel African retroviruses seem to be antigenically related to the simian T-cell lymphotropic virus (hereinafter "STLV-III") shown to be widely present in healthy African green monkeys and other simian species [Kanki et al. 1985]. This raises the possibility of a large group of African primate lentiviruses, ranging from the apparently non-pathogenic simian viruses to the LAV-type viruses. Their precise relationship will only be known after their complete genetic characterization, but it is already very likely that they have evolved from a common progenitor. The important genetic variability we have observed between isolates of the AIDS virus in Central Africa is probably a hallmark of this entire group and may account for the apparently important genetic divergence between its members (loss of cross-antigenicity in the envelopes). In this sense, the conservation of the tropism for the T4 lymphocytes suggests that it is a major advantage aquired by these retroviruses.

EXPERIMENTAL PROCEDURES

Virus Isolation $LAV_{ELI}$ was isolated from the peripheral blood lymphocytes of the patient as described [Barre-Sinoussi et al., 1983]. Briefly, the lymphocytes were fractionated and co-cultivated with phytohaemagglutinin-stimulated normal human lymphocytes in the presence of interleukin 2 and anti-alpha interferon serum. Viral production was assessed by cell-free reverse transcriptase (hereinafter "RT") activity assay in the cultures and by electron microscopy.

Molecular Cloning

Normal donor lymphocytes were acutely infected ($10^4$ cpm of RT activity/$10^6$ cells) as described [Barré-Sinoussi et al., 1983], and total DNA was extracted at the beginning of the RT activity peak. A lambda library using the L47-1 vector [Loenen and Brammar, 1982] was constructed by partial HindIII digestion of the DNA as already described [Alizon et al., 1984]. About $5.10^5$ plaques for $LAV_{ELI}$, obtained by in vitro packaging (Amersham), were plated on E. coli LA101 and screened in situ under stringent conditions, using the 9 kb SacI insert of the clone lambda J19 [Alizon et al., 1984] carrying most of the $LAV_{BRU}$ genome as probe. Clones displaying positive signals were plaque-purified and propagated on E. coli C600 recBC, and the recombinant phage E-H12 carrying the complete genetic information of $LAV_{ELI}$ was further characterized by restriction mapping.

Nucleotide Sequence Strategy

Viral fragments derived from E-H12 were sequenced by the dideoxy chain terminator procedure [Sanger et al., 1977] after "shotgun" cloning in the M13mp8 vector [Messing and Viera, 1982] as previously described [Sonigo et al., 1985]. The viral genome of $LAV_{ELI}$ is 9176 nucleotides long as shown in FIGS. 7A–7I. Each nucleotide of $LAV_{ELI}$ was determined from more than 5 independent clones on average.

Significance of the Figures

FIG. 1 contains an analysis of AIDS virus isolates, showing:

A/Restriction maps of the inserts of phage lambda clones derived from cells infected with $LAV_{ELI}$ (E-H12) and with $LAV_{MAL}$ (hereinfter "M-H11"). The schematic genetic organization of the AIDS virus has been drawn above the maps. The LTRs are indicated by solid boxes. Restriction sites are indicated as follows: A:AvaI; B:BamHI; Bg:BgIII; E:EcoRI; H:HindIII; Hc:HincII; K:KpnI; N:NdeI; P:PstI; S:SacI; and X:XbaI.

Asterisks indicate the HindIII cloning sites in lambda L47-1 vector.

B/A comparison of the sites for seven restriction enzymes in six isolates: the prototype AIDS virus $LAV_{BRU}$, $LAV_{MAL}$ and $LAV_{ELI}$; and Z1, Z2 and Z3. Restriction sites are represented by the following symbols vertically aligned wih the symbols in FIG. 1a: ●:BgIII; ★:EcoRI; ∇:HincII; ▼:HindIII; ♦:KpnI; ◊:NdeI; and ○:SacI.

FIG. 2 shows the genetic organization of the central region in AIDS virus isolates. Stop codons in each phase are represented as vertical bars. Vertical arrows indicate possible AUG initiation codons. Splice acceptor (A) and donor (D) sites identified in subgenomic viral mRNA [Muesing et al., 1985] are shown below the graphic of $LAV_{BRU}$, and corresponding sites in $LAV_{ELI}$ and $LAV_{MAL}$ are indicated. PPT indicates the repeat of the polypurine tract flanking the 3'LTR. As observed in $LAV_{BRU}$ [Wain-Hobson et al., 1985], the PPT is repeated 256 nucleotides 5' to the end of the pol gene in both the $LAV_{ELI}$ and $LAV_{MAL}$ sequences, but this repeat is degenerated at two positions in $LAV_{ELI}$.

FIG. 3 shows an alignment of the protein sequences of four AIDS virus isolates. Isolate $LAV_{BRU}$ [Wain-Hobson et al., 1985] is taken as reference; only differences with LAV$_{BRU}$ are noted for ARV 2 [Sanchez-Pescador et al., 1985] and the two Zairian isolates LAV$_{MAL}$ and LAV$_{ELI}$. A minimal number of gaps (−) were introduced in the alignments. The NH$_2$-termini of p$_{25}{}^{gag}$ and p18$^{gag}$ are indicated [Sanchez-Pescador, 1985]. The potential cleavage sites in the envelope precursor [Allan et al., 1985a; diMarzoVeronese, 1985] separating the signal peptide (hereinafter "SP"), OMP and TMP are indicated as vertical arrows; conserved cysteines are indicated by black circles and variable cysteines are boxed. The one letter code for each amino acid is as follows: A:Ala; C:Cys; D:Asp; E:Glu; F:Phe; G:Gly; H:His; I:Ile; K:Lys; L:Leu; M:Met; N:Asn; P:Pro; Q:Gln; R:Arg; S:Ser; T:Thr; V:Val; W:Trp; Y:Tyr.

FIG. 4 shows a quantitation of the sequence divergence between homologous proteins of different isolates. Part A of each table gives results deduced from two-by-two alignments using the proteins of LAV$_{BRU}$ as reference, part B, those of LAV$_{ELI}$ as reference. Sources: Muesing et al., 1985 for HTLV-3; Sanchez-Pescador et al., 1985 for ARV 2 and Wain-Hobson et al., 1985 for LAV$_{BRU}$. For each case in the tables, the size in amino acids of the protein (calculated from the first methionine residue or from the beginning of the orf for pol) is given at the upper left part. Below are given the number of deletions (left) and insertions (right) necessary for the alignment. The large numbers in bold face represent the percentage of amino acids substitutions (insertions/deletions being excluded). Two by two alignments were done with computer assistance [Wilburg and Lipman, 1983], using a gag penalty of 1, K-tuple of 1, and window of 20, except for the hypervariable domains of env, where the number of gaps was made minimum, and which are essentially aligned as shown in FIG. 3. The sequence of the predicted protein encoded by orf R of HTLV-3 has not been compared because of a premature termination relative to all other isolates.

FIG. 5 shows the variability of the AIDS virus envelope protein. For each position x of the alignment of env (FIG. 3), variability V(x) was calculated as: V(x)=number of different amino-acids at position x/frequency of the most abundant amino acid at position x. Gaps in the alignments are considered as another amino acid. For an alignment of 4 proteins, V(x) ranges from 1 (identical AA in the 4 sequences) to 16 (4 different AA). This type of representation has previously been used in a compilation of the AA sequence of immunoglobulins variable regions [Wu and Kabat, 1970]. Vertical arrows indicate the cleavage sites; asterisks represent potential N-glysosylation sites (N-X-S/T) conserved in all four isolates; black triangles represent conserved cysteine residues. Black lozanges mark the three major hydrophobic domains: OMP, TMP and SP; and the hyper-variable domains: Hyl, 2 and 3.

FIG. 6 shows the direct repeats in the proteins of different AIDS virus isolates. These examples are derived from the aligned sequences of gag (a, b), F (c, d) and env (e, f, g, h) shown in FIG. 3. The two elements of the direct repeat are boxed, while degenerated positions are underlined.

FIGS. 7A–7I show the complete cDNA sequence of LAV$_{ELI}$ of this invention.

The invention thus pertains more specifically to the proteins, glycoproteins and other polypeptides including the polypeptidic structures shown in the FIGS. 1–7. The first and last amino acid residues of these proteins, glycoproteins and polypeptides carry numbers computed from a first amino acid of the open-reading frames concerned, although these numbers do not correspond exactly to those of the LAV$_{ELI}$ proteins concerned, rather to the corresponding proteins of the LAV$_{BRU}$ or sequences shown in FIGS. 3A, 3B and 3C. Thus a number corresponding to a "first amino acid residue" of a LAV$_{ELI}$ protein corresponds to the number of the first amino-acyl residue of the corresponding LAV$_{BRU}$ protein which, in any of FIG. 3A, 3B or 3C, is in direct alignment with the corresponding first amino acid of the LAV$_{ELI}$ protein. Thus the sequences concerned can be read from FIGS. 7A–7I to the extent where they do not appear with sufficient clarity from FIGS. 3A–3F.

The preferred protein sequences of this invention extend between the corresponding "first" and "last" amino acid residues. Also preferred are the protein(s)- or glycoprotein(s)-portions including part of the sequences which follow:

OMP or gp110 proteins, including precursors:
1 to 530
OMP or gp110 without precursor:
34–530
Sequence carrying the TMP or gp41 protein:
531–877, particularly
680–700 well conserved stretches of OMP:
37–130,
211–289 and
488–530 well conserved stretch found at the end of the OMP and the beginning of TMP:
490–620.

Proteins containing or consisting of the "well conserved stretches" are of particular interest for the production of immunogenic compositions and (preferably in relation to the stretches of the env protein) of vaccine compositions against the LAV-1 viruses.

The invention concerns more particularly all the DNA fragments which have been more specifically referred to in the drawings and which correspond to open reading frames. It will be understood that one skilled in the art will be able to obtain them all, for instance by cleaving an entire DNA corresponding to the complete genome of LAV$_{ELI}$, such as by cleavage by a partial or complete digestion thereof with a suitable restriction enzyme and by the subsequent recovery of the relevant fragments. The DNA disclosed above can be resorted to also as a source of suitable fragments. The techniques disclosed in PCT application for the isolation of the fragments which can then be included in suitable plasmids are applicable here too. Of course, other methods can be used, some of which have been examplified in European Application No. 178,978, filed Sep. 17, 1985. Reference is for instance made to the following methods:

a) DNA can be transfected into mammalian cells with appropriate selection markers by a variety of techniques, such as calcium phosphate precipitation, polyethylene glycol, protoplast-fusion, etc.

b) DNA fragments corresponding to genes can be cloned into expression vectors for E. coli, yeast- or mammalian cells and the resultant proteins purified.

c) The proviral DNA can be "shot-gunned" (fragmented) into procaryotic expression vectors to generate fusion polypeptides. Recombinants, producing antigenically competent fusion proteins, can be identified by simply screening the recombinants with antibodies against LAV antigens.

The invention further refers to DNA recombinants, particularly modified vectors, including any of the preceding DNA sequences adapted to transform corresponding microorganisms or cells, particularly eucaryotic cells such as yeasts, for instance *Saccharomyces cerevisiae*, or higher eucaryotic cells, particularly cells of mammals, and to permit expression of said DNA sequences in the corresponding microorganisms or cells. General methods of that type have been recalled in the abovesaid PCT international patent aplication PCT/EP 85/00548, filed Oct. 18, 1985.

More particularly the invention relates to such modified DNA recombinant vectors modified by the abovesaid DNA sequences and which are capable of transforming higher eucaryotic cells particularly mammalian cells. Preferably, any of the abovesaid sequences are placed under the direct control of a promoter contained in said vectors and recognized by the polymerases of said cells, such that the first nucleotide codons expressed correspond to the first triplets of the above-defined DNA sequences. Accordingly, this invention also relates to the corresponding DNA fragments which can be obtained from the genome of $LAV_{ELI}$ or its cDNA by any appropriate method. For instance, such a method comprises cleaving said $LAV_{ELI}$ genome or its cDNA by restriction enzymes preferably at the level of restriction sites surrounding said fragments and close to the opposite extremities respectively thereof, recovering and identifying the fragments sought according to sizes, if need be checking their restriction maps or nucleotide sequences (or by reaction with monoclonal antibodies specifically directed against epitopes carried by the polypeptides encoded by said DNA fragments), and further if need be, trimming the extremities of the fragment, for instance by an exonucleolytic enzyme such as Bal31, for the purpose of controlling the desired nucleotid-sequences of the extremities of said DNA fragments or, conversely, repairing said extremities with Klenow enzyme and possibly ligating the latter to synthetic polynucleotide fragments designed to permit the reconstitution of the nucleotide extremities of said fragments. Those fragments may then be inserted in any of said vectors for causing the expression of the corresponding polypeptide by the cell transformed therewith. The corresponding polypeptide can then be recovered from the transformed cells, if need be after lysis thereof, and purified by methods such as electrophoresis. Needless to say, all conventional methods for performing these operations can be resorted to.

The invention also relates more specifically to cloned probes which can be made starting from any DNA fragment according to this invention, thus to recombinant DNAs containing such fragments, particularly any plasmids amplifiable in procaryotic or eucaryotic cells and carrying said fragments. Using the cloned DNA fragments as a molecular hybridization probe—either by labelling with radionucleotides or with fluorescent reagents—LAV virion RNA may be detected directly in the blood, body fluids and blood products (e.g. of the antihemophylic factors such as Factor VIII concentrates) and vaccines (e.g., hepatitis B vaccine). It has already been shown that whole virus can be detected in culture supernatants of LAV producing cells. A suitable method for achieving that detection comprises immobilizing virus on a support (e.g., a nitrocellulose filter), disrupting the virion and hybridizing with labelled (radiolabelled or "cold" fluorescent- or enzyme-labelled) probes. Such an approach has already been developed for Hepatitis B virus in peripheral blood [SCOTTO J. et al. Hepatology (1983), 3, 379–384].

Probes according to the invention can also be used for rapid screening of genomic DNA derived from the tissue of patients with LAV related symptoms, to see if the proviral DNA or RNA present in host tissue and other tissues can be related to that of $LAV_{ELI}$.

A method which can be used for such screening comprises the following steps: extraction of DNA from tissue, restriction enzyme cleavage of said DNA, electrophoresis of the fragments and Southern blotting of genomic DNA from tissues, subsequent hybridization with labelled cloned LAV proviral DNA. Hybridization in situ can also be used.

Lymphatic fluids and tissues and other non-lymphatic tissues of humans, primates and other mammalian species can also be screened to see if other evolutionnary related retrovirus exist. The methods referred to hereinabove can be used, although hybridization and washings would be done under non-stringent conditions.

The DNAs or DNA fragments according to the invention can be used also for achieving the expression of viral antigens of $LAV_{ELI}$ for diagnostic purposes.

The invention relates generally to the polypeptides themselves, whether synthesized chemically, isolated from viral preparations or expressed by the different DNAs of the invention, particularly by the ORFs or fragments thereof in appropriate hosts, particularly procaryotic or eucaryotic hosts, after transformation thereof with a suitable vector previously modified by the corresponding DNAs.

More generally, the invention also relates to any of the polypeptide fragments (or molecules, particularly glycoproteins having the same polypeptidic backbone as the polypeptides mentioned hereinabove) bearing an epitope characteristic of a protein or glycoprotein of $LAV_{ELI}$, which polypeptide or molecule then has N-terminal and C-terminal extremities respectively either free or, independently from each other, covalently bonded to amino acids other than those which are normally associated with them in the larger polypeptides or glycoproteins of the LAV virus, which last mentioned amino acids are then free or belong to another polypeptidic sequence. Particularly, the invention relates to hybrid polypeptides containing any of the epitope-bearing-polypeptides which have been defined more specifically hereinabove, recombined with other polypeptides fragments normally foreign to the LAV proteins, having sizes sufficient to provide for an increased immunogenicity of the epitope-bearing-polypeptide yet, said foreign polypeptide fragments either being immunogenically inert or not interfering with the immunogenic properties of the epitope-bearing-polypeptide.

Such hybrid polypeptides, which may contain from 5 up to 150, even 250 amino acids, usually consist of the expression products of a vector which contained ab initio a nucleic acid sequence expressible under the control of a suitable promoter or replicon in a suitable host, which nucleic acid sequence had however beforehand been modified by insertion therein of a DNA sequence encoding said epitope-bearing-polypeptide.

Said epitope-bearing-polypeptides, particularly those whose N-terminal and C-terminal amino acids are free, are also accessible by chemical synthesis according to technics well known in the chemistry of proteins.

The synthesis of peptides in homogeneous solution and in solid phase is well known. In this respect, recourse may be had to the method of synthesis in homogeneous solution described by Houbenweyl in the work entitled "Methoden der Organischen Chemie" (Methods of Organic Chemistry) edited by E. WUNSCH., vol. 15-I and II, THIEME, Stuttgart 1974. This method of synthesis consists of successively condensing either the successive amino acids in twos, in the appropriate order or successive peptide fragments previously available or formed and containing already several amino-acyl residues in the appropriate order respectively. Except for the carboxyl and aminogroups which will be engaged in the formation of the peptide bonds, care must be taken to protect beforehand all other reactive groups borne by these amino-acyl groups or fragments. However, prior to the formation of the peptide bonds, the carboxyl groups are advantageously activated, according to methods well known in the synthesis of peptides. Alternatively, recourse may be had to coupling reactions bringing into play conventional coupling reagents, for instance of the carbodiimide type, such as 1-ethyl-3-(3-dimethyl-amino-propyl)-carbodiimide. When the amino acid group used carries an additional amine group (e.g., lysine) or another acid function (e.g., glutamic acid), these groups may be protected by carbobenzoxy or t-butyloxycarbonyl groups, as regards the amine groups, or by t-butylester groups, as regards the carboxylic groups. Similar procedures are available for the protection of other reactive groups, for example, an —SH group (e.g., in cysteine) can be protected by an acetamidomethyl or paramethoxybenzyl group.

In the case of a progressive synthesis, amino acid by amino acid, the synthesis starts preferably with the condensation of the C-terminal amino acid with the amino acid which corresponds to the neighboring aminoacyl group in the desired sequence and so on, step by step, up to the N-terminal amino acid. Another preferred technique which can be used is that described by R. D. Merrifield in "Solid Phase Peptide Synthesis" [J. Am. Chem. Soc., 45, 2149–2154]. In accordance with the Merrifield process, the first C-terminal amino acid of the chain is fixed to a suitable porous polymeric resin, by means of its carboxylic group, the amino group of the amino acid then being protected, for example by a t-butyloxycarbonyl group. When the first C-terminal amino acid is thus fixed to the resin, the protective group of the amine group is removed by washing the resin with an acid, i.e., trifluoroacetic acid, when the protective group of the amine group is a t-butyloxycarbonyl group. Then, the carboxylic group of the second amino acid, which is to provide the second amino-acyl group of the desired peptidic sequence, is coupled to the deprotected amine group of the C-terminal amino acid fixed to the resin. Preferably, the carboxyl group of this second amino acid has been activated, for example by dicyclohexyl-carbodiimide, while its amine group has been protected, for example by a t-butyloxycarbonyl group. The first part of the desired peptide chain, which comprises the first two amino acids, is thus obtained. As previously, the amine group is then deprotected, and one can further proceed with the fixing of the next amino-acyl group and so forth until the whole peptide sought is obtained. The protective groups of the different side groups, if any, of the peptide chain so formed can then be removed. The peptide sought can then be detached from the resin, for example by means of hydrofluoric acid, and finally recovered in pure form from the acid solution according to conventional procedures.

As regards the peptide sequences of smallest size bearing an epitope or immunogenic determinant, and more particularly those which are readily accessible by chemical synthesis, it may be required, in order to increase their in vivo immunogenic character, to couple or "conjugate" them covalently to a physiologically acceptable and non-toxic carrier molecule. By way of examples of carrier molecules or macromolecular supports which can be used for making the conjugates according to the invention can be mentioned natural proteins, such as tetanic toxoid, ovalbumin, serum-albumins, hemocyanins, etc. Synthetic macromolecular carriers, for example polysines or poly(D-L-alanine)-poly(L-lysine)s, can be used too. Other types of macromolecular carriers that can be used, which generally have molecular weights higher than 20,000, are known from the literature. The conjugates can be synthesized by known processes such as are described by Frantz and Robertson in "Infect. and Immunity", 33, 193–198 (1981) and by P. E. Kauffman in "Applied and Environmental Microbiology", October 1981 Vol. 42, No. 4, pp. 611–614. For instance, the following coupling agents can be used: glutaric aldehyde, ethyl chloroformate, water-soluble carbodiimides such as(N-ethyl-N' (3-dimethylamino-propyl) carbodiimide, HCl), diisocyanates, bis-diazobenzidine, di- and trichloro-s-triazines, cyanogen bromides and benzaquinone, as well as the coupling agents mentioned in "Scand. J. Immunol.", 1978, vol. 8, pp. 7–23 (Avrameas, Ternynck, Guesdon).

Any coupling process can be used for bonding one or several reactive groups of the peptide, on the one hand, and one or several reactive groups of the carrier, on the other hand. Again coupling is advantageously achieved between carboxyl and amine groups carried by the peptide and the carrier or vice-versa in the presence of a coupling agent of the type used in protein synthesis, e.g., 1-ethyl-3-(3-dimethylaminopropyl)-carbodiimide, N-hydroxybenzotriazole, etc. Coupling between amine groups respectively borne by the peptide and the carrier can also be made with glutaraldehyde, for instance, according to the method described by BOQUET, P. et al. (1982) Molec. Immunol., 19, 1441–1549, when the carrier is hemocyanin.

The immunogenicity of epitope-bearing-peptides can also be reinforced by oligomerisation thereof, for example in the presence of glutaraldehyde or any other suitable coupling agent. In particular, the invention relates to the water soluble immunogenic oligomers thus obtained, comprising particularly from 2 to 10 monomer units.

The glycoproteins, proteins and other polypeptides (generally designated hereinafter as "antigens" of this invention) whether obtained by methods, such as are disclosed in the earlier patent applications referred to above, in a purified state from $LAV_{ELI}$ virus preparations or—as concerns more particularly the peptides by chemical synthesis, are useful in processes for the detection of the presence of anti-LAV antibodies in biological media, particularly biological fluids such as sera from man or animal, particularly with a view of possibly diagnosing LAS or AIDS.

Particularly the invention relates to an in vitro process of diagnosis making use of an envelope glycoprotein or of a polypeptide bearing an epitope of this glycoprotein of $LAV_{ELI}$ for the detection of anti-LAV antibodies in the serums of persons who carry them. Other polypeptides—particular those carrying an epitope of a core protein—can be used too.

A preferred embodiment of the process of the invention comprises:

depositing a predetermined amount of one or several of said antigens in the cups of a titration microplate;

introducing increasing dilutions of the biological fluid, to be diagnosed (e.g., blood serum, spinal fluid, lymphatic fluid, and cephalo-rachidian fluid), into these cups;

incubating the microplate;

washing carefully the microplate with an appropriate buffer;

adding into the cups specific labelled antibodies directed against blood immunoglobulins and detecting the antigen-antibody-complex formed, which is then indicative of the presence of LAV antibodies in the biological fluid.

Advantageously the labelling of the anti-immunoglobulin antibodies is achieved by an enzyme selected from among those which are capable of hydrolysing a substrate, which substrate undergoes a modification of its radiation-absorption, at least within a predetermined band of wavelenghts. The detection of the substrate, preferably comparatively with respect to a control, then provides a measurement of the potential risks, or of the effective presence, of the disease.

Thus, preferred methods of immuno-enzymatic and also immunofluorescent detections, in particular according to the ELISA technique, are provided. Titrations may be determinations by immunofluorescence or direct or indirect immuno-enzymatic determinations. Quantitative titrations of antibodies on the serums studied can be made.

The invention also relates to the diagnostic kits themselves for the in vitro detection of antibodies against the LAV virus, which kits comprise any of the polypeptides identified herein and all the biological and chemical reagents, as well as equipment, necessary for peforming diagnostic assays. Preferred kits comprise all reagents required for carrying out ELISA assays. Thus preferred kits will include, in addition to any of said polypeptides, suitable buffers and anti-human immunoglobulins, which anti-human immunoglobulins are labelled either by an immunofluorescent molecule or by an enzyme. In the last instance, preferred kits also comprise a substrate hydrolysable by the enzyme and providing a signal, particularly modified absorption of a radiation, at least in a determined wavelength, which signal is then indicative of the presence of antibody in the biological fluid to be assayed with said kit.

It can of course be of advantage to use several proteins or polypeptides not only of $LAV_{ELI}$, but also of $LAV_{MAL}$ together with homologous proteins or polypeptides of earlier described viruses, such as $LAV_{BRU}$, HTLV-3, ARV 2, etc.

The invention also relates to vaccine compositions whose active principle is to be constituted by any of the antigens, i.e., the hereinabove disclosed polypeptides of $LAV_{ELI}$, particularly the purified gp110 or immunogenic fragments thereof, fusion polypeptides or oligopeptides in association with a suitable pharmaceutically or physiologically acceptable carrier. A first type of preferred active principle is the gp110 immunogen of said immunogens. Other preferred active principles to be considered in that fields consist of the peptides containing less than 250 amino acid units, preferably less than 150, particularly from 5 to 150 amino acid residues, as deducible for the complete genome of $LAV_{ELI}$ and even more preferably those peptides which contain one or more groups selected from Asn-X-Thr and Asn-X-Ser as defined above. Preferred peptides for use in the production of vaccinating principles are peptides (a) to (f) as defined above. By way of example, there may be mentioned that suitable dosages of the vaccine compositions are those which are effective to elicit antibodies in vivo, in the host, particularly a human host. Suitable doses range from 10 to 500 micrograms of polypeptide, protein or glycoprotein per kg, for instance 50 to 100 micrograms per kg.

The different peptides according to this invention can also be used themselves for the production of antibodies, preferably monoclonal antibodies specific for the respective different peptides. For the production of hybridomas secreting said monoclonal antibodies, conventional production and screening methods can be used. These monoclonal antibodies, which themselves are part of the invention, provide very useful tools for the identification and even determination of relative proportions of the different polypeptides or proteins in biological samples, particularly human samples containing LAV or related viruses.

The invention further relates to the hosts (procaryotic or eucaryotic cells) which are transformed by the above mentioned recombinants and which are capable of expressing said DNA fragments.

Finally the invention also concerns vectors for transforming eucaryotic cells of human origin, particularly lymphocytes, the polymerase of which are capable of recognizing the LTRs of LAV. Particularly said vectors are characterized by the presence of a LAV LTR therein, said LTR being then active as a promoter enabling the efficient transcription and translation in a suitable host of a DNA insert coding for a determined protein placed under its controls.

Needless to say, the invention extends to all variants of genomes and corresponding DNA fragments (ORFS) having substantially equivalent properties, all of said genomes belonging to retroviruses which can be considered as equivalents of $LAV_{ELI}$. It must be understood that the claims which follow are also intended to cover all equivalents of the products (glycoproteins, polypeptides, DNAs, etc.) whereby an equivalent is a product, e.g., a polypeptide, which may distinguish from a product defined in any of said claims, say through one or several amino acids, while still having substantially the same immunological or immunogenic properties. A similar rule of equivalency shall apply to the DNAs, it being understood that the rule of equivalency will then be tied to the rule of equivalency pertaining to the polypeptides which they encode.

It will also be understood that all the literature referred to hereinbefore and hereinafter and all patent applications and patents not specifically identified herein but which form counterparts of those specifically designated herein, must be considered as incorporated herein by reference.

It should further be mentioned that the invention further relates to immunogenic compositions that contain preferably one or more of the polypeptides, which are specifically identified above and which have the amino acid sequences of $LAV_{ELI}$ that have been identified, or peptidic sequences corresponding to previously defined LAV proteins. In this respect, the invention relates more particularly to the particular polypeptides which have the sequences corresponding more specifically to the $LAV_{BRU}$ sequences which have been referred to earlier, i.e., the sequences extending between the following first and last amino acids, of the $LAV_{BRU}$ proteins themselves, i.e., the polypeptides having sequences contained in the $LAV_{BRU}$ OMP or $LAV_{BRU}$ TMP or sequences extending over both, particularly those extending from between the following positions of the amino acids included in the env open reading frame of the $LAV_{BRU}$ genome,

1–530

34–530 and more preferably

531–877, particularly 680–700,

37–130

211–289

488–530

490–620.

These different sequences can be used for any of the above defined purposes and in any of the compositions which have been disclosed.

Finally the invention also relates to the different antibodies which can be formed specifically against the different peptides which have been disclosed herein, particularly to the monoclonal antibodies which recognize them specifically. The corresponding hybridomas which can be formed starting from spleen cells previously immunized with such peptides which are fused with appropriate myeloma cells and selected according to standard procedures also form part of the invention.

Phage λ clone E-H12 derived from LAV$_{ELI}$ infected cells has been deposited at the CNCM under No. I-550 on May 9, 1986. Phage clone M-H11 derived from LAV$_{MAL}$ infected cells has been deposited at the CNCM under No. I-551 on May 9, 1986.

REFERENCES

Alizon, M., Sonigo, P., Barré-Sinoussi, F., Chermann, J. C., Tiollais, P., Montagnier, L. & Wain-Hobson, S. (1984). Molecular cloning of lymphadenopathy-associated virus. Nature 312, 757–760.

Allan, J. S., Coligan, J. E., Barin, F., McLane, M. F., Sodroski, J. G., Rosen, C. A., Haseltine, W. A., Lee, T. H., & Essex, M. (1985a). Major glycoprotein antigens that induce antibodies in AIDS patients. Science 228, 1091–1094.

Allan, J. S., Coligan, J. E., Lee, T. H., McLane, M. F., Kanki, P. J., Groopman, J. E., & Essex, M. (1985b). A new HTLV-III/LAV antigen detected by antibodies from AIDS patients. Science 230, 810–813.

Arya, S. K., Guo, C., Josephs, S. F., & Wong-Staal, F. (1985). Trans-activator gene of human T-lymphotropic virus type III (HTLV-III). Science 229, 69–73.

Bailey, A. C., Downing, R. G., Cheinsong-Popov, R., Tedder, R. C., Dalgleish, A. G., & Weiss, R. A. (1985). HTLV-III serology distinguishes atypical and endemic Kaposi's sarcoma in Africa. Lancet I, 359–361.

Barin, F., M'Boup, S., Denis, F., Kanki, P., Allan, J. S., Lee, T. M., & Essex, M. (1985). Serological evidence for virus related to simian T lymphotropic retrovirus in residents of West Africa. Lancet II, 1387–1389.

Barré-Sinoussi, F., Chermann, J. C., Rey, F., Nugeyre, M. T., Chamaret, S., Gruest, J., Dauguet, C., Axler-Blin, C., Brun-Vézinet, F., Rouzioux, C., Rozenbaum, W. & Montagnier, L. (1983). Isolation of a T-lymphotropic retrovirus from a patient at risk of acquired immune deficiency syndrome (AIDS). Science 220, 868–870.

Been, S., Rutledge, R., Folks, T., Gold, J., Baker, L. McCormick, J. Feorino, P., Piot, P., Quinn T. & Martin, M. (1985). Genomic heterogeneity of AIDS retroviral isolates from North America and Zaire. Science 230, 949–951.

Borst, P., & Cross, G. A. M. (1982). Molecular basis for trypanosome antigenic variation. Cell 29, 291–303.

Brun-Vésinet, F., Rouzioux, C., Montagnier, L., Chamaret, S., Gruest, J., Barré-Sinoussi, F., Geroldi, D., Chermann, J. C., McCormick, J. Mitchell, S., Piot, P., Taelmann, H. Minlangu, K. B., Wobin, O., Mbendi, N. Mazebo, P., Kalambayi, K. Bridts, C., Desmyter, J., Feinsod, F., & Quinn T. C. (1984). Prevelance of antibodies to lymphadenopathy-associated virus in African patients with AIDS. Science 226, 453–456.

Chang, N. T., Chanda, P. K., Barone, A. D., McKinney, S., Rhodes, D. P., Tam, S. H., Shearman, C. W., Huang, J. & Chang, T. W. (1985). Expression in *Escheridia coli* of open reading frame gene segments of HTLV-III. Science 228, 93–96.

Chiu, I. M., Yaniv, A., Dahlberg, J. E., Gazit, A., Skuntz, S. F., Tronick, S. R. & Aaronson, S. A. (1985). Nucleotide sequence evidence for relationship of AIDS retrovirus to lentiviruses. Nature 317, 366–368.

Clark, S. P., & Mak, T. W., (1984). Fluidity of a retrovirus genome. J. Virol. 50, 759–765.

Clavel, F., Klatzmann, D., & Montagnier, L., (1985). Deficient neutralizing capacity of sera from patients with AIDS or related syndromes. Lancet I, 879–880.

Clavel, F., Brun-Vézinet, F., Guetard, D., Chamaret, S., Laurent, A., Rouzioux, C., Rey, M., Katlama, C., Rey, F., Champelinaud, J. L., Nina, J. S., Mansinho, K., Santos-Ferreira, M. O., Klatzmann, D., & Montagnier, L. (1986). LAV type II: a second retrovirus associated with AIDS in West-Africa. C.R. Acad. Sci. Paris 302, 485–488.

Clements, J. E., Narayan, O., Griffin, D. E. and Johnson, R. T. (1980). genomic changes associated with antigenic variation of visna virus during persistent infection. Proc. Natl. Acad. Sci. USA 77, 4454–4458.

Clumeck, N., Sonnet, J., Taelman, M., Mascart-Lemone, F., De Bruyére, M., Van de Perre, P., Dasnoy, J., Marcelis, L., Lamy, M., Jonas, C., Eyckmans, L., Noel, H., Vanhaeverbeek, M. & Butzler, J. P. (1984). Acquired immune deficiency syndrome in African patients. N. Engl. J. Med., 10, 492–497.

Dalgleish, A. G., Beverley, P. C., Clapham P. R., Crawford, D. H., Greaves, M. F. & Weiss, R. A. (1984). The CD4; (T4) antigen is an essential component of the receptor for the AIDS retrovirus. Nature 312, 763–767.

Darlix, J. L. (1986) Control of Rous sarcoma virus RNA translation and packaging by the 5' and 3' untranslated sequences. J. Mol. Biol., in the press.

DeLarco, J. & Todaro, G. J. (1976). Membrane receptors of murine leukemia viruses: characterization using the purified viral envelope glycoprotein, gp71. Cell 8, 365–371.

DiMarzoVeronese, F., DeVico, A. L., Copeland, T. D., Oroszlan, S., Gallo, R. C., & Sarngadharan, M. G. (1985). Characterization of gp 41 as the transmembrane protein coded by the HTLV-III/LAV envelope gene. Science 229, 1403–1405.

Ellrodt, A., Barré-Sinoussi, F., Le Bras, P., Nugeyre, M. T., Brun-Vézinet, F., Rouzioux, C., Segond, P., Caquet, R., Montagnier, L. & Chermann, J. C. (1984). Isolation of human T-lymphotropic retrovirus (LAV) from Zairan married couple, one with AIDS, one with prodromes. Lancet I, 1383–1385.

Hahn, B. H., Shaw, G. M., Arya, S. U., Popovic, M., Gallo, R. C., & Wong-Staal, F. (1984). Molecular cloning and characterizaion of the HTLV-III virus associated with AIDS. Nature 312, 166–169.

Holland, J., Spindler, K., Horodyski, F., Grabau, E., Nichol, S., & Van de Pol, S. (1982). Rapid evolution of RNA genomes. Science 215, 1577–1585.

Kan, N. C., Franchini, G., Wong-Staal, F., Dubois, G. C., Robey, W. G., Lautenberger, J. A., & Papas, T. S. (1986). Identification of HTLV-III/LAV sor gene product and detection of antibodies in human sera. Science 231, 1553–1555.

Kanki, P. J., Alroy, J. & Essex, M. (1985). Isolation of T-lymphotropic retroviruses from wild-caught African Green Monkeys. Science 230, 951–954.

Kanki, P. J., Barin, F., M'Boup, S., Allan, J. S., Romet-Lemonne, J. L., Markink, R., McLane, M. F., Lee, T. H., Arbeille, B., Denis, F. & Essex, M. (1986). New human T-lymphotropic retrovirus related to simian T-lymphotropic virus type III (STLV-III ). Science, 232, 238–243.

Klatzmann, D., Champagne, E., Chamaret, S., Gruest, J., Guetard, D., Hercend, T., Gluckman, J. C., & Montagnier, L. (1984). T-lymphocyte T4 molecule behave as the receptor for human retrovirus LAV. Nature 312, 767–768.

Kyte, J. & Doolittle, R., (1982). A simple methof for displaying the hydropathic character of a protein. J. Mol. Biol. 157, 105–132.

Koch, W., Hunsmann, G. & Friedrich, R. (1983). Nucleotide sequence of the envelope gene of Friend murine leukemia virus. J. Virol., 45, 1–9.

Lee, T. H., Coligan, J. E. Allan, J. S., McLane, M. F., Groopman, J. E. & Essex, M. (1986). A new HTLV III/LAV protein encoded by a gene found in cytopathic retroviruses. Science 231, 1546–1549.

Loenec, W. A. M. & Brammar, W. J. (1980). A bacteriophage lambda vector for cloning large DNA fragments made with several restriction enzymes. Gene 10, 249–259.

Lutley, R., Petursson, G., Palsson, P. A., Georgsson, G., Klein, J., & Nathanson, N, (1983). Antigenic drift in visna: virus variation during longterm infection of icelandic sheep. J. Gen. Virol. 64, 1433–1440.

MacDougal, J. S., Kennedy, M. S., Sligh, J. M., Cort, S. P., Mawle, A. & Nicholson, J. K. A. (1986). Binding of HTLV-III/LAV to T4+ cells by a complex of the 110 k viral protein and the T4 molecule. Science 231, 382–385.

Messing, J. and Viera, J. (1982). A new pair of M13 vectors for selecting either DNA strand of double digest restriction fragments. Gene 19, 269–276.

Montagnier, L. (1985). Lymphadenopathy-associated virus: from molecular biology to pathogenicity. Ann. Inter. Med. 103, 689–693.

Montagnier, L., Clavel, F., Krust, B., Chamaret, S., Rey, F., Barré-Sinoussi, F. & Chermann, J. C. (1985). Identification and antigenicity of the major envelope glycoprotein of lymphadenopathy-associated virus. Virology 144, 283–289.

Montelaro, R. C., Parekh, B., Orrego, A. & Issel, C. J. (1984). Antigenic variation during persistent infection by equine infectious anemia virus, a retrovirus. J. Biol. Chem., 250, 10539–10544.

Muesing, M. A., Smith, D. M., Cabradilla, C. D., Benton, C. V., Lasky, L. A. & Capon, D. J. (1985). Nucleic acid structure and expression of the human AIDS/lymphadenopathy retroviruses. Nature 313, 450–458.

Norman, C. (1985). Politics and science clash on African AIDS. Science 230, 1140–1142.

Piot, P., Quinn, T. C., Taelman, H., Feinsod, F. M., Minlangu, K. B., Wobin, O., Mbendi, N., Mazebo, P., Ndongi, K., Stevens, W., Kalambayi, K., Mitchell, S., Bridts, C. & McCormick, J. B. (1984). Acquired immunodeficiency syndrome in Power, M. D., Marx, P. A., Bryant, M. L., Gardner, M. B., Barr, P. J. & Luciw, P. A. (1986). Nucleotide sequence of SRV-1, a type D simian acquired immune deficiency syndrome retrovirus. Science 231, 1567–1572.

Rabson, A. B. & Martin, M. A. (1985). Molecular organization of the AIDS retrovirus. Cell 40, 477–480.

Ratner, L., Haseltine, W., Patarca, R., Livak, K. J., Starcich, B., Josephs, S. F., Doran, E. R., Rafalski, A., Whitchorn, E. A., Baumeister, K., Ivanoff, L., Petteway, S. R., Pearson, M. L., Lautenbergen, J. A., Papas, T. S., Ghrayeb, J., Chang, N. T., Gallo, R. C. & Wong-Staal, F. (1985). Complete nucleotide sequence of the AIDS virus, HTLV-III. Nature 313, 277–284.

Robinson, P. J. G., Hunsmann, G., Schneider, J. & Schirrmacher, V. (1980). Possible cell surface receptor for Friend murine leukemia virus is isolated with viral envelop glycoprotein complexes. J. Virol., 36, 291–294.

Rosen, C. A., Sodroski, J. G. & Haseltine, W. A. (1985). The location of cisacting regulatory sequences in the human T cell lymphotropic virus type III (HTLV-III/LAV) long terminal repeat. Cell 41, 813–823.

Sanchez-Pescador, R. Power, M. D., Barr, P. J., Steimer, K. S., Stemfieib, M. M., Brown-Shimer, S. L., Gee, W. W., Bernard, A., Randolph, A., Levy, J. A., Dina, D. & Luciw, P. A., (1985). Nucleotide sequence and expression of an AIDS-associated retrovirus (ARV-2). Science 227, 484–492.

Sanger, F., Nicklen, S. & Coulsen, A. R. (1977). DNA sequencing with chain terminating inhibitors. Proc. Natl. Acad. Sci. USA 74, 5463–5467.

Scott, J. V., Stowring, L., Haase, A. T., Narayan, O. & Vigne, R. (1979). Antigenic variation in visna virus. Cell 18, 321–327.

Shimotohno, K., & Temin, H. (1982). Spontaneous variation and synthesis in the U3 region of the long terminal repeat of an avian retrovirus. J. Virol. 41, 163–171.

Sodroski, J., Patarca, R., Rosen C., Wong-Staal, F. & Haseltine, W. (1985). Location of the trans-activating region of the genome of human T-cell lymphotropic virus type II. Science 229, 74–77.

Sonigo, P., Alizon, M., Staskus, K., Klatzmann, D., Cole, S., Danos, O., Retzel, E., Tiollais, P., Haase, A. & Wain-Hobson, S. (1985). Nucleotide sequence of the visna lentivirus: Relationship to the AIDS virus. Cell 42, 369–382.

Sonigo, P., Barker, C., Hunter, E. & Wain-Hobson S. (1986). Nucleotide sequence of Mason-Pfizer Monkey virus: an immunosuppressive D-type retrovirus. Cell, in the press.

Steinhauer, D. A., & Holland, J. H. (1986). Direct method for quantitation of extreme polymerase error frequencies at selected single base in viral RNA. J. Virol. 57, 219–228.

Thormar, H., Barshatsky, M. R., Arnesen, K., & Kozlowski, P. B. (1983). The emergence of antigenic variants is a rare event in long-term visna virus invention in vivo. J. Gen. Virol. 64, 1427–1432.

Van de Perre, P., Rouvroy, D., Lepage, P., Bogaerts, J., Kestelyn, P., Kayihigi, J., Hekker, A. C., Butzler, J. P. & Clumeck, N. (1984). Acquired immunodeficiency syndrome in Rwanda. Lancet II, 62–65.

Varmus, H. & Swanstrom, R. (1984). Replication of retroviruses. In Molecular biology of the tumor viruses/RNA tumor viruses. R. Weiss, N. Teich, H. Varmus, J. Coffin, eds. (Cold Spring Harbor Laboratory, New York), vol. 1, pp. 369–512.

Wain-Hobson, S., Sonigo, P., Danos, O., Cole, S., & Alizon, M. (1985). Nucleotide sequence of the AIDS virus, LAV. Cell 40, 9–17.

Webster, R. G., Laver, W. G., Air, G. M. & Schild, G. C. (1982). Molecular mechanisms of variation in influenza viruses. Nature 296, 115–121.

Weiss, R. A. (1984). Human T-cell retroviruses. In Molecular biology of the tumor viruses: RNA viruses. R. Weiss, N. Teich, H. Varmus, J. Coffin, eds. (Cold Spring Harbor Laboratory, New York), vol II: supplement, pp. 405–485.

Weiss, R. A., Clapham, P. R., Cheinson-Popov, R. Dalgleish, A. G., Carne, C. A., Weller, I. A. D. & Tedder, R. C. (1985). Neutralization of human T-lymphotropic virus type III by sera of AIDS and AIDS-risk patients, Nature, 316, 69–72.

Wilburg, W. J., & Lipman, D. J. (1983). Rapid similarity searches of nucleic acid and protein data banks. Proc. Natl. Acad. Sci. USA 80, 726–730.

Wu, T. T., & Kabat, E. A. (1970). An analysis of the sequences of the variable regions of Bence-Jones proteins and myeloma light chains and their implications for antibody complementarity. J. Exp. Med. 132, 211–250.

The invention claimed is:

1. A purified HIV-1 virus,
   wherein said virus encodes an HIV-$1_{ELI}$ variant Env protein containing the well-conserved stretches of OMP at amino acid positions 37–130, 211–289, and 488–530 of HIV-1$_{ELI}$ or HIV-1$_{MAL}$ shown in FIG. 3E.

2. The purified virus of claim 1,
wherein said HIV-1$_{ELI}$ variant Env protein has the following amino acid residues at positions 37–130:
LWVTVYYGVPVWKEATTTLFCASDAKSY-ETEAHNIWATHACVPTDPNPQEIALE NVTENFN-MWKNNMVEQMHEDIISLWDQSLK-PCVKLTPLCV.

3. The purified virus of claim 1,
wherein said HIV-1$_{ELI}$ variant Env protein has the following amino acid residues at positions 211–289:
CNTSAITQACPKVSFEPIPIHYCAPAG-FAILKCRDKKFNGTGPCTNVSTVQCTHG IRPV-VSTQLLLNGSLAEEEVIIRS.

4. The purified virus of claim 1,
wherein said HIV-1$_{ELI}$ variant Env protein has the following amino acid residues at positions 488–530:
RPGGGDMRDNWRSELYKYKVV-QIEPLGVAPTRAKRRVVEREKR.

5. The purified virus of claim 1,
wherein said HIV-1$_{ELI}$ variant Env protein has the following amino acid residues at positions 37–130, 211–289, and 488–530:
LWVTVYYGVPVWKEATTTLFCASDAKSY-ETEAHNIWATHACVPTDPNPQEIALE NVTENFN-MWKNNMVEQMHEDIISLWDQSLK-PCVKLTPLCV;
CNTSAITQACPKVSFEPIPIHYCAPAG-FAILKCRDKKFNGTGPCTNVSTVQCTHG IRPV-VSTQLLLNGSLAEEEVIIRS; and
RPGGGDMRDNWRSELYKYKVV-QIEPLGVAPTRAKRRVVEREKR.

* * * * *